United States Patent
Wersland et al.

(10) Patent No.: US 11,559,462 B2
(45) Date of Patent: *Jan. 24, 2023

(54) PERCUSSIVE MASSAGE DEVICE AND METHOD OF USE

(71) Applicant: Therabody, Inc., Los Angeles, CA (US)

(72) Inventors: Jason Wersland, Manhattan Beach, CA (US); Benjamin Nazarian, Los Angeles, CA (US); Jaime Sanchez Solana, Los Angeles, CA (US); Harald Quintus-Bosz, Boston, MA (US); Anthony Parker, Boston, MA (US); Chris McCaslin, San Francisco, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/515,097

(22) Filed: Oct. 29, 2021

(65) Prior Publication Data
US 2022/0047452 A1 Feb. 17, 2022

Related U.S. Application Data

(63) Continuation of application No. 17/167,672, filed on Feb. 4, 2021, now Pat. No. 11,160,722, which is a (Continued)

(51) Int. Cl.
*A61H 23/00* (2006.01)
*A61H 23/02* (2006.01)
(Continued)

(52) U.S. Cl.
CPC ....... *A61H 23/006* (2013.01); *A61H 15/0085* (2013.01); *A61H 23/00* (2013.01);
(Continued)

(58) Field of Classification Search
CPC .......... A61H 1/00; A61H 1/006; A61H 1/008; A61H 23/00; A61H 23/004; A61H 23/006;
(Continued)

(56) References Cited

U.S. PATENT DOCUMENTS 1,545,027 A 7/1925 Ashlock
1,657,765 A 1/1928 Pasque
(Continued)

FOREIGN PATENT DOCUMENTS

CN 2788807 6/2006
CN 201524220 U 7/2010
(Continued)

OTHER PUBLICATIONS

TheraGun device in YouTube video "TheraGun: What It Does," https://www.youtube.com/watch?v=FB_JTZnD7vs Aug. 24, 2016 (upload date).
(Continued)

*Primary Examiner* — Colin W Stuart
(74) *Attorney, Agent, or Firm* — Sterne, Kessler, Goldstein & Fox P.L.L.C.

(57) ABSTRACT

A percussive massage device that includes a housing, an electrical source, a motor positioned in the housing, a switch for activating the motor, and a push rod assembly operatively connected to the motor and configured to reciprocate in response to activation of the motor. The housing includes first, second and third handle portions that cooperate to define a handle opening, wherein the first handle portion defines a first axis, the second handle portion defines a second axis and the third handle portion defines a third axis, and wherein the first, second and third axes cooperate to form a triangle.

16 Claims, 32 Drawing Sheets

Related U.S. Application Data continuation of application No. 16/919,588, filed on Jul. 2, 2020, now Pat. No. 10,918,565, which is a continuation of application No. 16/675,772, filed on Nov. 6, 2019, now Pat. No. 10,702,448, which is a continuation-in-part of application No. 16/357,984, filed on Mar. 19, 2019, now Pat. No. 10,912,707, which is a continuation of application No. 15/920,322, filed on Mar. 13, 2018, now Pat. No. 10,357,425, which is a continuation-in-part of application No. 15/458,920, filed on Mar. 14, 2017, now abandoned.

(60) Provisional application No. 62/899,098, filed on Sep. 11, 2019, provisional application No. 62/844,424, filed on May 7, 2019, provisional application No. 62/785,151, filed on Dec. 26, 2018.

(51) Int. Cl.

| | | |
|---|---|---|
| *A61H 15/00* | (2006.01) | |
| *B27B 19/00* | (2006.01) | |
| *A61H 1/00* | (2006.01) | |
| *B23D 51/16* | (2006.01) | |
| *B23D 49/10* | (2006.01) | |
| *B23D 49/00* | (2006.01) | |
| *B27B 19/02* | (2006.01) | |
| *A61B 17/14* | (2006.01) | |

(52) U.S. Cl.
CPC ........ *A61H 23/0254* (2013.01); *A61B 17/142* (2016.11); *A61H 1/008* (2013.01); *A61H 2023/029* (2013.01); *A61H 2201/0165* (2013.01); *A61H 2201/12* (2013.01); *A61H 2201/123* (2013.01); *A61H 2201/1207* (2013.01); *A61H 2201/1215* (2013.01); *A61H 2201/14* (2013.01); *A61H 2201/149* (2013.01); *A61H 2201/1481* (2013.01); *A61H 2201/1664* (2013.01); *B23D 49/007* (2013.01); *B23D 49/10* (2013.01); *B23D 51/16* (2013.01); *B27B 19/00* (2013.01); *B27B 19/002* (2013.01); *B27B 19/02* (2013.01)

(58) Field of Classification Search
CPC ................ A61H 23/02; A61H 23/0218; A61H 23/0254; A61H 23/0263; A61H 23/04; A61H 23/06; A61H 2023/002; A61H 2023/0209; A61H 2023/0272; A61H 2023/0281; A61H 2023/029; A61H 39/00; A61H 39/002; A61H 39/007; A61H 39/04; A61H 2201/0165; A61H 2201/12; A61H 2201/1207; A61H 2201/1215; A61H 2201/1223; A61H 2201/123; A61H 2201/1238; A61H 2201/14; A61H 2201/1408; A61H 2201/1418; A61H 2201/1481; A61H 2201/149; A61H 2201/1664; B23D 51/16; B23D 49/162; B23D 49/165; B23D 49/00; B23D 49/007; B23D 49/008; B23D 49/10; B23D 49/16; B23D 49/167; B26D 7/2621; B26D 7/2614; B26D 5/14; B27B 19/00; B27B 19/002; B27B 19/006; B27B 19/09; B27B 19/02; A61B 17/148; A61B 17/142; A61B 17/14; A61B 17/144; B25B 13/00; B25B 13/06; B25B 23/00; B25B 23/0007; B25B 23/0035; B25B 23/0057
See application file for complete search history.

(56) References Cited

U.S. PATENT DOCUMENTS

| | | |
|---|---|---|
| D91,454 S | 2/1934 | Decker |
| D93,943 S | 11/1934 | Rand |
| D118,980 S | 2/1940 | Larson |
| D129,045 S | 8/1941 | Wilhide |
| D161,484 S | 1/1951 | McQuown |
| D163,324 S | 5/1951 | Rittenhouse |
| D180,923 S | 9/1957 | Anton |
| D181,742 S | 12/1957 | Madl |
| 2,931,632 A | 4/1960 | Angelis |
| D195,145 S | 4/1963 | Ernest |
| D197,142 S | 12/1963 | Godfrey |
| 3,172,675 A | 3/1965 | Gonzalez |
| D207,505 S | 4/1967 | Whitman |
| 3,452,226 A | 6/1969 | Hettich |
| 3,545,301 A | 12/1970 | Richter |
| 3,626,934 A | 12/1971 | Andis |
| D237,454 S | 11/1975 | Adams |
| D237,455 S | 11/1975 | Schramm |
| 3,942,251 A | 3/1976 | Griffies |
| 4,150,668 A | 4/1979 | Johnston |
| 4,173,217 A | 11/1979 | Johnston |
| D265,985 S | 8/1982 | House |
| 4,549,535 A | 10/1985 | Wing |
| 4,566,442 A | 1/1986 | Mabuchi |
| D287,814 S | 1/1987 | Hiraishi |
| D292,368 S | 10/1987 | Mikiya |
| 4,730,605 A | 3/1988 | Noble |
| D300,132 S | 3/1989 | Culbertson |
| 4,815,224 A | 3/1989 | Miller |
| D303,373 S | 9/1989 | Ching, Jr. |
| D310,005 S | 8/1990 | Precht |
| D314,320 S | 2/1991 | Brosius |
| D320,379 S | 10/1991 | Culbertson |
| D321,338 S | 11/1991 | Sakamoto |
| 5,085,207 A | 2/1992 | Fiore |
| D329,166 S | 9/1992 | Doggett |
| D329,291 S | 9/1992 | Wollman |
| D334,012 S | 3/1993 | Chen |
| D338,802 S | 8/1993 | Maass |
| D345,077 S | 3/1994 | Maass |
| D345,727 S | 4/1994 | Flowers |
| D345,888 S | 4/1994 | Joss |
| D349,029 S | 7/1994 | Matsunaga |
| 5,417,644 A | 5/1995 | Lee |
| D363,352 S | 10/1995 | Huen |
| D367,712 S | 3/1996 | Young |
| D374,934 S | 10/1996 | Lie |
| 5,569,168 A | 10/1996 | Hartwig |
| 5,573,500 A | 11/1996 | Katsunuma |
| D383,366 S | 9/1997 | Heck |
| D383,435 S | 9/1997 | Svetlik |
| D384,639 S | 10/1997 | Kawakami |
| D387,728 S | 12/1997 | Kawakami |
| D388,175 S | 12/1997 | Lie |
| D397,991 S | 9/1998 | Kawakami |
| D400,161 S | 10/1998 | Nagele |
| D400,758 S | 11/1998 | Hippen |
| 5,910,197 A * | 6/1999 | Chaconas ............... B25B 13/06 81/177.85 |
| D412,485 S | 8/1999 | Kato |
| 5,951,501 A | 9/1999 | Griner |
| D417,648 S | 12/1999 | Clowers |
| D425,014 S | 5/2000 | Willkens |
| D430,774 S | 9/2000 | Naft |
| D432,077 S | 10/2000 | Zurwelle |
| D433,300 S | 11/2000 | Buck |
| D440,136 S | 4/2001 | Buck |
| 6,228,042 B1 | 8/2001 | Dungan |
| D474,445 S | 5/2003 | Matsuoka |
| D475,595 S | 6/2003 | Hatch |
| D475,679 S | 6/2003 | Cooper |
| D476,746 S | 7/2003 | Harris |
| 6,599,260 B2 | 7/2003 | Tucek |
| D478,385 S | 8/2003 | Dirks |
| D481,279 S | 10/2003 | Buck |

(56) References Cited

U.S. PATENT DOCUMENTS

| | | |
|---|---|---|
| 6,663,657 B1 | 12/2003 | Miller |
| 6,682,496 B1 | 1/2004 | Pivaroff |
| 6,723,060 B2 | 4/2004 | Miller |
| D504,111 S | 4/2005 | Ozawa |
| D510,317 S | 10/2005 | Sun |
| D530,270 S | 10/2006 | Ozawa |
| D531,733 S | 11/2006 | Burout |
| D544,102 S | 6/2007 | Pivaroff |
| D544,436 S | 6/2007 | Kawahara |
| D547,264 S | 7/2007 | Kondo |
| D553,562 S | 10/2007 | Okada |
| D575,224 S | 8/2008 | Taniguchi |
| D579,868 S | 11/2008 | Harrison |
| D580,353 S | 11/2008 | Harrison |
| D587,977 S | 3/2009 | Waldron |
| D593,204 S | 5/2009 | Manke |
| D597,482 S | 8/2009 | Kondo |
| D604,235 S | 11/2009 | Tarter |
| D605,586 S | 12/2009 | Tong |
| D622,660 S | 8/2010 | Taniguchi |
| D631,315 S | 1/2011 | Kue |
| 7,927,259 B1 | 4/2011 | Rix |
| 7,996,996 B2 | 8/2011 | Hirabayashi |
| D666,303 S | 8/2012 | Ding |
| 8,342,187 B2 | 1/2013 | Kalman |
| D682,195 S | 5/2013 | Aglassinger |
| 8,646,348 B2 | 2/2014 | Hung |
| D703,480 S | 4/2014 | Lownds |
| D722,016 S | 2/2015 | Beukema |
| 8,951,216 B2 | 2/2015 | Yoo |
| D726,495 S | 4/2015 | Ryan |
| D740,222 S | 10/2015 | Tang |
| D776,612 S | 1/2017 | Chen |
| 9,889,066 B2 | 2/2018 | Danby |
| D817,869 S | 5/2018 | Lee |
| D826,418 S | 8/2018 | Lad |
| 10,201,470 B2 | 2/2019 | Griner |
| D842,489 S | 3/2019 | Spewock |
| 10,276,844 B2 | 4/2019 | Wackwitz |
| D855,822 S | 8/2019 | Marton |
| D858,432 S | 9/2019 | Altenburger |
| D862,382 S | 10/2019 | Altenburger |
| D866,790 S | 11/2019 | Lee |
| D867,279 S | 11/2019 | Altenburger |
| D877,351 S | 3/2020 | Wersland |
| D884,205 S | 5/2020 | Zhuang |
| 10,702,448 B2 | 7/2020 | Wersland |
| D893,738 S | 8/2020 | Zhuang |
| 10,857,064 B2 | 12/2020 | Wersland |
| 10,918,565 B2 | 2/2021 | Wersland |
| 10,959,911 B2 | 3/2021 | Wersland |
| D919,560 S | 5/2021 | Taniguchi |
| 2001/0016697 A1 | 8/2001 | Gorsen |
| 2003/0009116 A1 | 1/2003 | Luettgen |
| 2003/0094356 A1 | 5/2003 | Waldron |
| 2003/0144615 A1 | 7/2003 | Lin |
| 2003/0195443 A1 | 10/2003 | Miller |
| 2005/0252011 A1 | 11/2005 | Neumeier |
| 2006/0025710 A1 | 2/2006 | Schulz |
| 2006/0123941 A1 | 6/2006 | Wadge |
| 2006/0192527 A1 | 8/2006 | Kageler |
| 2007/0144310 A1 | 6/2007 | Pozgay |
| 2007/0150004 A1 | 6/2007 | Colloca |
| 2008/0103419 A1 | 5/2008 | Adamson |
| 2008/0314610 A1 | 12/2008 | Meixner |
| 2010/0145242 A1 | 6/2010 | Tsai |
| 2010/0298863 A1* | 11/2010 | Hindinger ............ A61N 1/3603 606/204 |
| 2012/0253245 A1 | 10/2012 | Stanbridge |
| 2013/0138023 A1 | 5/2013 | Lerro |
| 2013/0261516 A1 | 10/2013 | Cilea |
| 2013/0281897 A1 | 10/2013 | Hoffmann |
| 2014/0024982 A1 | 1/2014 | Doyle |
| 2014/0180331 A1 | 6/2014 | Turner |
| 2015/0005682 A1 | 1/2015 | Danby |
| 2015/0148592 A1 | 5/2015 | Kanbar |
| 2015/0375315 A1 | 12/2015 | Ukai |
| 2016/0367425 A1 | 12/2016 | Wersland |
| 2017/0156974 A1 | 6/2017 | Griner |
| 2017/0304144 A1* | 10/2017 | Tucker .................. A61H 23/00 |
| 2017/0304145 A1 | 10/2017 | Pepe |
| 2018/0236572 A1 | 8/2018 | Ukai |
| 2019/0254921 A1 | 8/2019 | Marton |
| 2019/0337140 A1* | 11/2019 | Shanklin ............. B25B 23/0021 |
| 2019/0350793 A1 | 11/2019 | Wersland |
| 2020/0085675 A1 | 3/2020 | Lee |

FOREIGN PATENT DOCUMENTS

| | | | |
|---|---|---|---|
| CN | 201743890 U | | 2/2011 |
| CN | 201847899 U | | 6/2011 |
| CN | 203598194 U | | 5/2014 |
| CN | 104352341 | | 7/2016 |
| JP | 1990019157 | | 1/1990 |
| JP | 1992047440 | | 4/1992 |
| JP | H04-047440 U | * | 4/1992 |
| JP | 1995051393 | | 2/1995 |
| JP | 003077837 | | 6/2001 |
| JP | 2005204777 | | 4/2005 |
| JP | 2010534110 | | 11/2010 |
| KR | 200313149 Y1 | | 5/2003 |
| KR | 101123926 | | 4/2012 |
| KR | 101406275 | | 6/2014 |
| TW | 201440753 A | | 8/2015 |
| WO | 2015038005 | | 3/2005 |
| WO | 2009014727 | | 1/2009 |
| WO | 2014118596 | | 8/2014 |

OTHER PUBLICATIONS

TheraGun device in Archive.org webpage https://web.archive.org/web/20151218063848/http://www.theragun.com/#intro-1 Dec. 18, 2015 (archive date).

TheraGun G1 device in YouTube video "Theragun G1: Product Overview," https://www.youtube.com/watch?v=m9ilhfMGfZ8 Apr. 18, 2017 (upload date).

TheraGun G2Pro device in YouTube video "The Theragun G2PRO: Revolutionary Percussive Therapy," https://www.youtube.com/watch?v=2p9R6VA798o Oct. 10, 2017 (upload date).

JP2018-517683 Office Action dated Oct. 25, 2018.

CA 2990178 Office Action dated Oct. 25, 2018.

International Search Report and Written Opinion issued in PCT/US18/22426.

Rachel [no family name indicated], "Jigsaw Massager", Apr. 18, 2010 (https://web.archive.org/web/20100418041422/http://www.instructables.com/id/Jigsaw-Massager/).

Rockwell Trans4mer Operating Manual for Multi-purpose saw, Model RK2516/RK2516K, 2011.

Worx Trans4mer "Safety and Operating Manual" for 12V Li-Ion Multi-purposed saw, WX540, WX540.3, 2013.

PCT/US2016/038326 International Search Report & Written Opinion dated Sep. 1, 2016.

AU 2016284030 Examination Report dated May 7, 2018.

* cited by examiner

PERCUSSIVE MASSAGE DEVICE AND METHOD OF USE

CROSS-REFERENCE TO RELATED APPLICATIONS

This application is a continuation of U.S. patent application Ser. No. 17/167,672, filed Feb. 4, 2021, which is a continuation of U.S. patent application Ser. No. 16/919,588, filed Jul. 2, 2020, now U.S. Pat. No. 10,918,565, which is a continuation of U.S. patent application Ser. No. 16/675,772, filed Nov. 6, 2019, now U.S. Pat. No. 10,702,448, which is a continuation-in-part of U.S. patent application Ser. No. 16/357,984, filed Mar. 19, 2019, now U.S. Pat. No. 10,912,707, which is a continuation of U.S. patent application Ser. No. 15/920,322, filed on Mar. 13, 2018, now U.S. Pat. No. 10,357,425, which is a continuation-in-part of U.S. patent application Ser. No. 15/458,920, filed on Mar. 14, 2017. U.S. patent application Ser. No. 16/675,772 also claims the benefit of U.S. Provisional Patent Application No. 62/785,151, filed on Dec. 26, 2018, U.S. Provisional Patent Application No. 62/844,424, filed on May 7, 2019, and U.S. Provisional Patent Application No. 62/899,098, filed on Sep. 11, 2019. All applications listed above are hereby incorporated by reference in their entireties.

FIELD OF THE INVENTION

The present invention relates generally to massage devices and more particularly to a vibrating massage device or percussive massage device that provides reciprocating motion.

BACKGROUND OF THE INVENTION

Massage devices often provide ineffective massages that are superficial and do not provide any real benefit. Accordingly, there is a need for an improved massage device.

SUMMARY OF THE PREFERRED EMBODIMENTS

In accordance with a first aspect of the present invention there is provided a method of using a percussive massage device that includes obtaining the percussive massage device that includes a housing having first, second and third handle portions that cooperate to define a handle opening, an electrical source, a motor positioned in the housing, a switch for activating the motor, and a push rod assembly operatively connected to the motor and configured to reciprocate in response to activation of the motor. The method also includes activating the motor using the switch, grasping the first handle portion, massaging a first body part, alternatively grasping the second handle portion and massaging the first body part, and alternatively grasping the third handle portion and massaging the first body part. In a preferred embodiment, the first handle portion defines a first axis, the second handle portion defines a second axis and the third handle portion defines a third axis, and the first, second and third axes cooperate to form a triangle. In a preferred embodiment, the method also includes grasping the second handle portion, massaging a second body part, grasping the third handle portion, and massaging a third body part.

In accordance with another aspect of the present invention there is provided percussive massage device that includes a housing, an electrical source, a motor positioned in the housing, a switch for activating the motor, and a push rod assembly operatively connected to the motor and configured to reciprocate in response to activation of the motor. In a preferred embodiment, the housing includes first, second and third handle portions that cooperate to define a handle opening, wherein the first handle portion defines a first axis, the second handle portion defines a second axis and the third handle portion defines a third axis, and wherein the first, second and third axes cooperate to form a triangle.

Preferably, the first handle portion includes a first handle portion interior edge and defines a first handle portion length and the first handle portion length is long enough that when a user grasps the first handle portion with a hand at least a portion of three fingers extend through the handle opening and contact the first handle portion interior edge. Preferably, the second handle portion includes a second handle portion interior edge and defines a second handle portion length and the second handle portion length is long enough that when a user grasps the second handle portion with a hand at least a portion of three fingers extend through the handle opening and contact the second handle portion interior edge. Preferably, the third handle portion includes a third handle portion interior edge and defines a third handle portion length and the third handle portion length is long enough that when a user grasps the third handle portion with a hand at least a portion of three fingers extend through the handle opening and contact the third handle portion interior edge. In a preferred embodiment, the first handle portion is generally straight, the second handle portion is generally straight and the third handle portion is generally straight. Generally straight means that the majority of the handle portion is straight, but can include rounded edges or corners where the different handle portions meet or where the handle portions meet the bulge portion or the finger protrusion, etc.

In a preferred embodiment, the switch includes switch electronics associated therewith, the electrical source is a battery that is housed in the second handle portion and the switch electronics are housed in the first handle portion. Preferably, the motor is configured to rotate a pinion shaft having a pinion gear thereon about a shaft rotation axis. The housing includes a gear member disposed therein that is operatively engaged with the pinion gear and rotates about a gear rotation axis. The push rod assembly is operatively connected to the gear member, and rotational motion of the pinion shaft is converted to reciprocating motion of the push rod assembly through the engagement of the pinion gear and the gear member. The motor includes a motor shaft extending outwardly therefrom and a pinion coupling assembly is positioned between the motor shaft and the pinion shaft. The pinion coupling includes a lower connector that is operatively connected to the motor shaft, an upper connector that is operatively connected to the pinion shaft, and a cross coupling positioned between the lower connector and the upper connector. In a preferred embodiment, the lower connector includes a main body portion that defines a central opening that receives the motor shaft and first and second lower connector arms extending outwardly from the main body portion, the upper connector includes a main body portion that defines a central opening that receives the pinion shaft and first and second upper connector arms extending outwardly from the main body portion, the cross coupling includes radially extending ribs, and the first and second lower connector members and the first and second upper connector members operatively engage the radially extending ribs. Preferably, the lower and upper connectors comprise a plastic and the cross coupling comprises an elastomer.

In a preferred embodiment, the gear member is disposed in a rotation housing that is rotatable between at least first and second positions. A gearbox housing that houses the gear member is disposed in the rotation housing. The gearbox housing includes a clearance slot having first and second ends defined therein. The push rod assembly extends through the clearance slot, such that when the rotation housing is rotated from the first position to the second position the push rod assembly moves within the clearance slot from adjacent the first end to adjacent the second end.

In a preferred embodiment, the push rod assembly includes a first rod portion having a proximal end and a distal end and a second rod portion having a proximal end and a distal end. The proximal end of the first rod portion is operatively connected to the motor. An adapter assembly is positioned between the first and second rod portions. The adapter assembly allows the first rod portion to pivot with respect to the second rod portion. Preferably, the adapter assembly includes an adapter member that includes a pocket that receives the distal end of the first rod portion therein. A pivot pin spans the pocket and extends through the distal end of the first rod portion. In a preferred embodiment, the adapter member includes a protrusion that is received in the proximal end of the second rod portion.

In accordance with another aspect of the present invention there is provided a massage device that includes a housing, an electrical input, a motor, a switch in electrical communication with the electrical input and the motor and configured to selectively provide power from the electrical input to the motor, an actuated output operatively connected to the motor and configured to reciprocate in response to activation of the motor, and a treatment structure operatively connected to a distal end of the actuated output. The actuated output is configured to reciprocate the treatment structure at a frequency of between about 15 Hz and about 100 Hz, and at an amplitude of between about 0.15 and about 1.0 inches. The combination of amplitude and frequency provides efficient reciprocation of the treatment structure such that the treatment structure provides therapeutically beneficial treatment to a targeted muscle of a user.

In a preferred embodiment, the actuated output is configured to reciprocate the treatment structure at a frequency of between about 25 Hz and about 48 Hz, and at an amplitude of between about 0.23 and about 0.70 inches. In another preferred embodiment, the actuated output is configured to reciprocate the treatment structure at a frequency of between about 33 Hz and about 42 Hz, and at an amplitude of between about 0.35 and about 0.65 inches.

In a preferred embodiment, the motor is configured to rotate a shaft having a shaft gear thereon about a shaft rotation axis. The housing includes a gear member disposed therein that is operatively engaged with the shaft gear and rotates about a gear rotation axis. The actuated output is operatively connected to the gear member, and the rotational motion of the shaft is converted to reciprocating motion of the actuated output through the engagement of the shaft gear and the gear member. Preferably, the gear rotation axis is perpendicular to the shaft rotation axis and an eccentric interface is disposed on the gear member at a location other than the gear rotation axis. Preferably, the device further includes a reciprocator shaft operatively connected to the eccentric interface, and a containment member. A head of the reciprocator shaft is contained by the containment member to restrict motion of the reciprocator shaft to a linear motion that is perpendicular to the gear rotation axis. In a preferred embodiment, the gear member comprises a counterweight disposed on the gear member, and the center of mass of the counterweight is not on the gear rotation axis. Preferably, the head of the reciprocator shaft includes an elongated opening therein, the eccentric interface includes a pin, and the pin is configured to move within the elongated opening as the gear member rotates.

In a preferred embodiment, the massage device includes a rotation housing. The main housing includes a rotation space defined therein. The rotation housing includes a main body portion disposed in the housing and an arm portion extending through the rotation space and outside the housing, wherein the actuated output extends outwardly from the arm portion, and the rotation housing can rotate within the rotation space between a plurality of positions. Preferably, the massage device includes a button extending outwardly from the housing that is movable between a first position and a second position. The button includes a plurality of teeth members. The housing includes a plurality of first teeth spaces defined therein and the rotation housing includes a plurality of second teeth spaces defined therein. When the button is in the first position the teeth members engage the first teeth spaces and the rotation housing cannot rotate. When the button is in the second position (when it is pressed in and overcomes the spring bias) the teeth members engage the second teeth spaces and the rotation housing can rotate.

In accordance with another aspect of the present invention, there is provided a reciprocating treatment device that includes a housing, a handle disposed on the housing, the handle having a handle axis, a motor disposed in the housing, and an actuated output operably connected to the motor. The actuated output is configured to reciprocate in response to activation of the motor. The reciprocation is along a reciprocation axis. The motor includes a shaft having a shaft rotation axis, and the shaft rotation axis lies in a plane defined by the handle axis and the reciprocation axis (they are all coplanar).

In a preferred embodiment, the reciprocating treatment device includes a gearbox to convert rotary motion from the shaft to reciprocal motion at the actuated output. Preferably, the gearbox includes a gear member having a gear rotation axis perpendicular to the shaft rotation axis, and an eccentric interface disposed on the gear at a location other than the gear rotation axis. The device also includes a reciprocator shaft operatively connected to the eccentric interface, and a reciprocator interface configured to restrict linear motion of the reciprocator shaft to a direction parallel to the reciprocation axis and perpendicular to the gear rotation axis. The gear member preferably includes a counterweight disposed on the gear member. The center of mass of the counterweight is not on the gear rotation axis.

In a preferred embodiment, the counterweight has a mass similar to the components of the reciprocating treatment device that reciprocate along the reciprocation axis. Preferably, the counterweight has a mass between 45 grams and 55 grams. In a preferred embodiment, the gearbox is connected to a compliant dampening block and the compliant dampening block is connected to the housing. Preferably, the compliant dampening block comprises a polymer. In a preferred embodiment, the shaft is operably connected with the gearbox through a compliant shaft damper.

An embodiment provides a reciprocal treatment device. The reciprocal treatment device includes a housing, a motor connected to the housing, and an actuated output. The housing includes a handle located on the housing. The handle has a handle axis. The actuated output is operably connected to the motor. The actuated output is configured to reciprocate in response to activation of the motor. Reciprocation of the actuated output is along a reciprocation axis.

The motor includes a shaft having a shaft rotation axis. The shaft rotation axis is parallel to a plane in which the handle axis and the reciprocation axis are located. Other embodiments of a reciprocal treatment device are also described.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
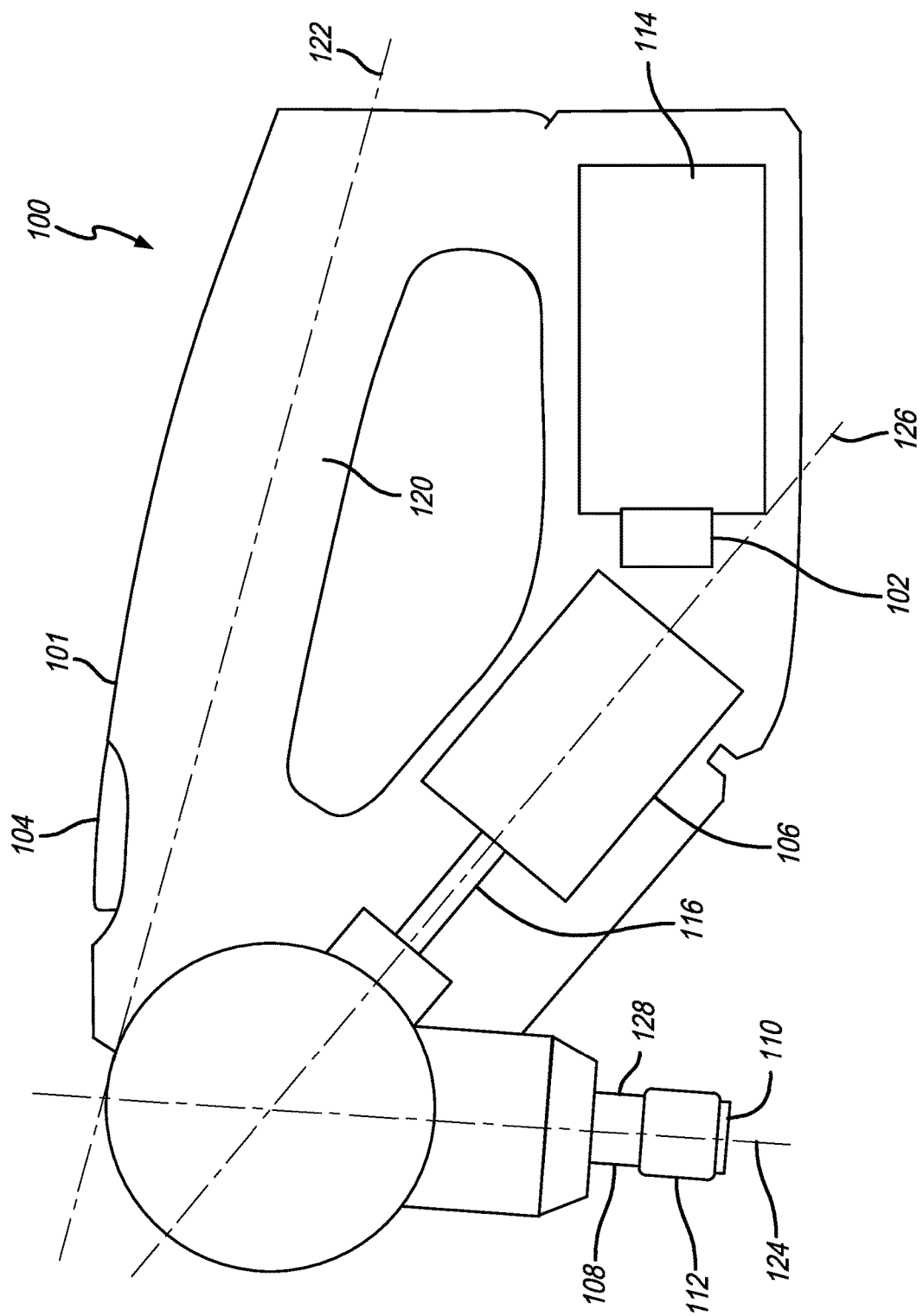
FIG. 1 depicts a cutaway side view of one embodiment of a reciprocating treatment device.

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

While many embodiments are described herein, at least some of the described embodiments provide an apparatus, system, and method for a reciprocating treatment device.

FIGS. 1-12 show embodiments of a reciprocating treatment device 100. FIGS. 1-4 show the device in schematic form and FIGS. 7-12 show the device 100 in more detail.

Figure 7:
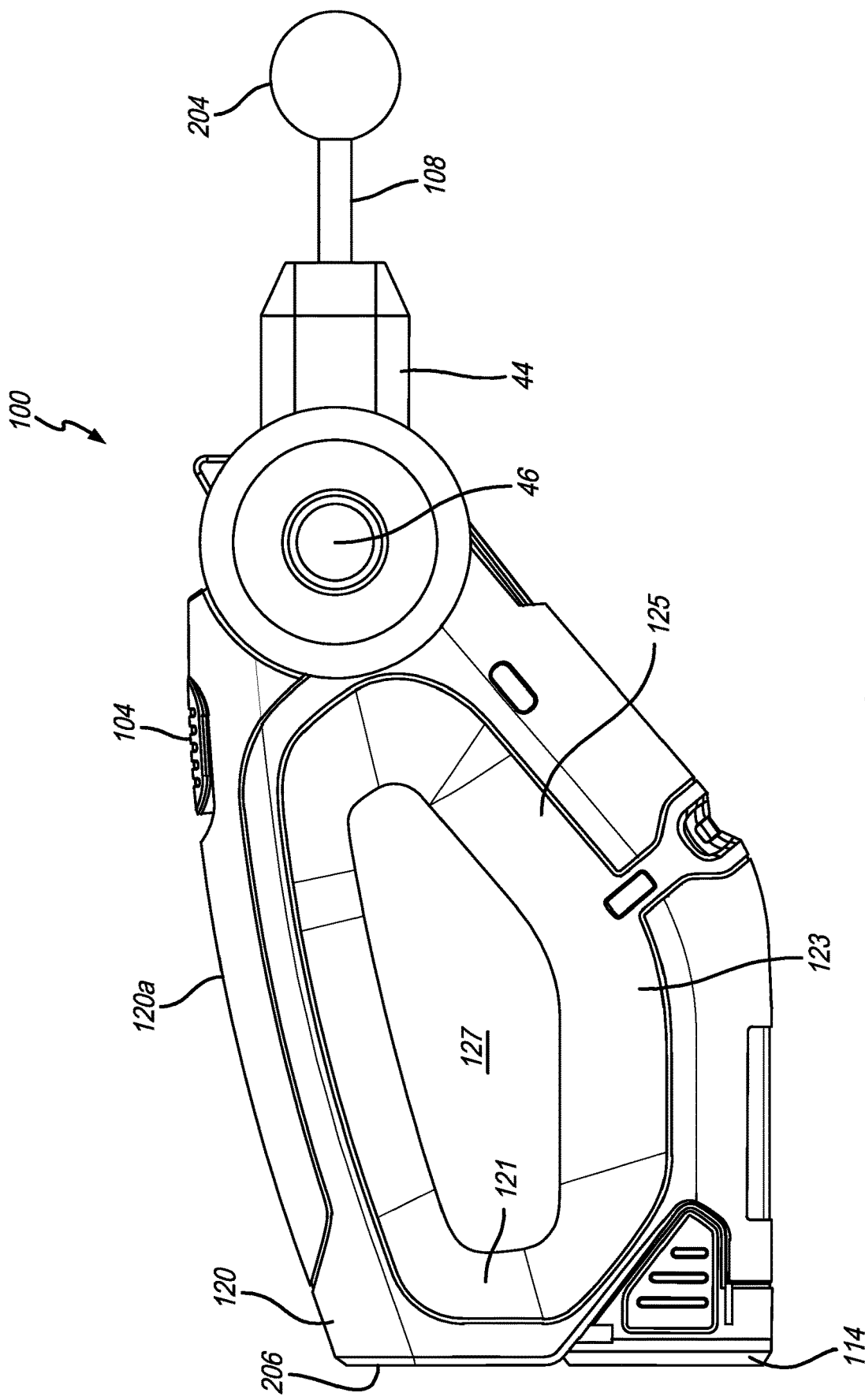
FIG. 7 is a side elevational view of a reciprocating treatment device in accordance with an embodiment of the present invention.
Figure 8:
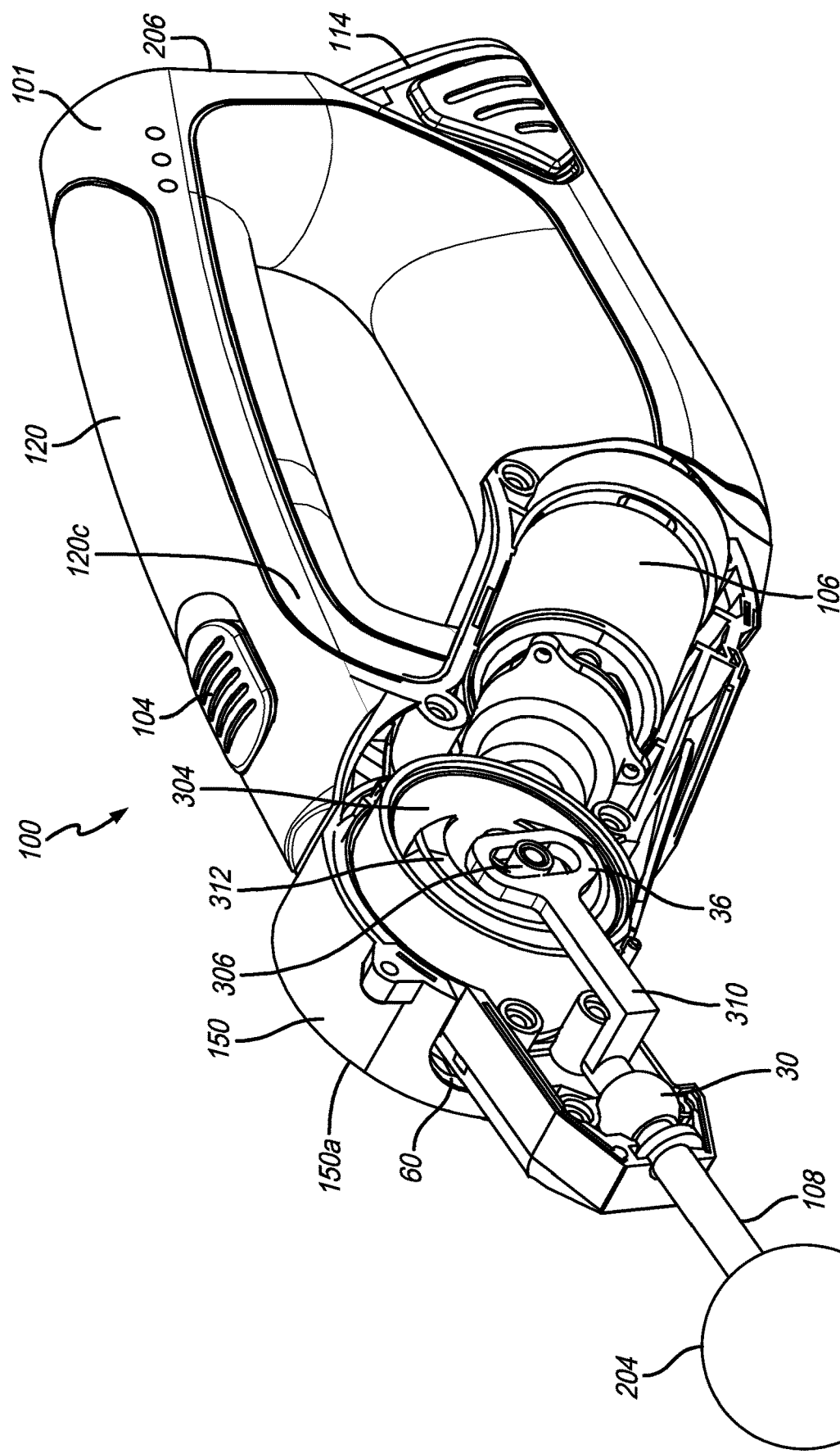
FIG. 8 is a perspective view of the reciprocating treatment device of FIG. 7 with a portion of the housing removed to show the motor and actuation components.

FIG. 1 depicts a cutaway side view of one embodiment of a reciprocating treatment device 100. Reference is also made to FIGS. 7-8. The reciprocating treatment device 100 includes a housing 101, a power input 102, a switch 104, a motor 106, and an actuated output 108. The reciprocating treatment device 100, in some embodiments, generates motion at the actuated output 108 for treating a patient.

The housing 101, in one embodiment, is a structure allowing for connection of one or more other components of the reciprocating treatment device 100. The housing 101 may completely or substantially enclose one or more other components. For example, the housing 101 may be a formed structure with attachment points for other components that substantially encloses one or more of those components when assembled. In another embodiment, the housing 101 may allow other components to be exposed. For example, the housing 101 may be an open frame. In some embodiments, the housing 101 encloses one or more components of the reciprocating treatment device 101 and leaves one or more other components of the reciprocating treatment device 101 exposed.

Figure 6:
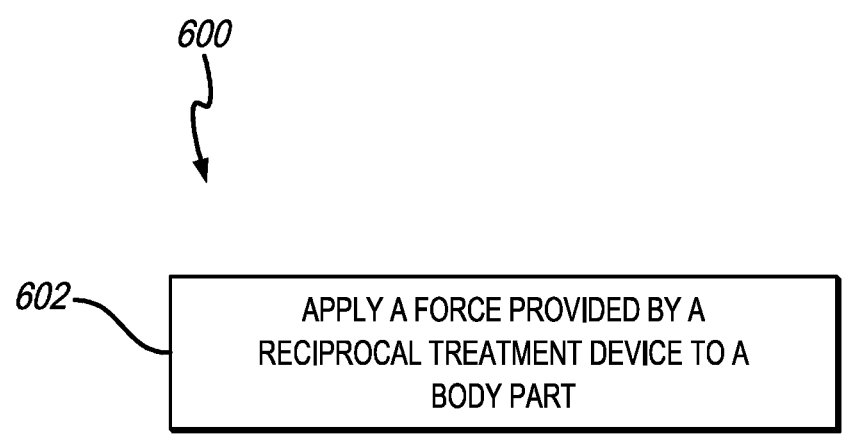
FIG. 6 depicts a flowchart diagram showing one embodiment of a method of use of the reciprocating treatment device of FIG. 1.

As shown in FIGS. 1, 6 and 7, the housing 101 includes a handle 120. The handle 120 defines a handle axis 122 that runs substantially along the longest dimension of the handle 120. In some embodiments, the handle 120 is straight or substantially straight along its longest dimension, and the handle axis 122 runs through the center or substantially through the center of the handle 120. In another embodiment, the handle 120 is curved along its longest dimension, and the handle axis 122 is tangent to the curvature of the handle 120 at the midpoint of the handle 120. In a preferred embodiment, the handle 120 has a top surface 120a that is shaped that it can be ergonomically gripped by a persons palm. This provides comfort for a user when operating the device. See, for example, U.S. Pat. No. 6,105,891, the entirety of which is incorporated herein by reference, which teaches a fishing reel knob that includes a similar shape that conforms to the user's palm. As shown in FIG. 7, the housing 101 includes the handle 120, a rear portion 121, and a lower portion 123 that includes an upwardly angled neck 125, that extends toward the bulge portion 150. The handle 120, rear portion 121, and lower portion 123 (including the neck 125) define a central opening 127

The power input 102, in some embodiments, is configured to receive a power input from a power source 114. The power source 114 may be any type of power source capable of supplying power to the motor 106. In one embodiment, the power input 102 receives an electrical input from the power source 114. For example, the power source 114 may be a battery that provides electrical current. In one embodiment, the battery is a rechargeable battery. In some embodiments, the battery is attachable to the reciprocating treatment device 100 such that the reciprocating treatment device 100 including the power source 114 is portable and cordless. In an alternative embodiment, the reciprocating treatment device 100 uses an external battery pack as a power source 114.

The battery may be any type of battery known in the art. For example, the battery may include a rechargeable lithium-ion (LiIon) based battery. In another example, the battery may include a rechargeable nickel metal hydride (NiMH) battery. In yet another example, the battery may include a rechargeable lithium-polymer (LiPo) battery. In some embodiments, the battery includes a nickel-cadmium (NiCad) battery. In one embodiment, the battery uses a non-rechargeable battery.

In an alternative embodiment, the power input 102 includes a cord to receive power from an electrical grid. For example, the reciprocating treatment device 100 may include a cord with a plug configured to interface with a wall socket to provide power.

In another alternative embodiment, the power input 102 is non-electrical. For example, the power input 102 may receive pressurized air from a pressure vessel or a network of pressurized air. In another embodiment, the power input 102 may include one or more reactive materials to provide energy for operation of the reciprocating treatment device 100.

The switch 104, in some embodiments, controls delivery of power to the motor 106. The switch 104 may be an electrical switch configured to allow passage of electric current when activated. In some embodiments, the switch 104 is a binary on/off switch. In another embodiment, the switch 104 is a variable switch. A variable switch controls the amount of power delivered to the motor 106. A relatively high amount of power delivered to the motor 106 by the variable switch 104 results in an increased speed of the motor 106. Are relatively low amount of power delivered to the motor 106 by the variable switch 104 results in a decreased speed of the motor 106. In one embodiment, the variable switch 104 includes a variable resistor that allows a progressively increased amount of power to flow to the motor 106 in response to a progressively increasing activation of that switch 104.

In some embodiments, the switch 104 may remain in an activated position in response to a user releasing the switch 104. In an alternate embodiment, the switch 104 may return to a deactivated position in response to a user releasing the switch 104. For example, the switch 104 may include a biasing member such as a spring configured to push the switch 104 to the deactivated position in response to the switch 104 being released.

In certain embodiments, the switch 104 includes multiple positions. For example, the switch 104 may include an off position, a first activated position, and a second activated position. The switch 104 may include one or more positions in which without additional user input, the switch 104 remains in that position, and one or more positions in which without additional user input, the switch 104 is biased to exit that position.

For example, the switch 104 may have an "off" position, an "on" position, and a "turbo" position. The "on" and "turbo" positions may activate reciprocation at different rates, such as 2300 cycles per minute in the "on" position and 2800 cycles per minute in the "turbo" position. Upon being set to the "on" position, the switch 104 may remain in the "on" position without requiring the user to maintain contact with the switch 104. Upon being set to the "turbo" position, the switch 104 may be biased to return to the "on" position unless the user maintains a force on the switch 104 that opposes a return to the "on" position.

The motor 106, in one embodiment, converts power from the power source 102 into motion. In some embodiments, the motor 106 is an electric motor. The electric motor may be any type of electric motor known in the art, including, but not limited to, a brushed motor, a brushless motor, a direct current (DC) motor, an alternating current (AC) motor, a mechanical-commutator motor, an electronic commutator motor, or an externally commutated motor.

In some embodiments, the motor 106 operates at a speed that can be varied by different levels of activation of the switch 104. For example, the motor 106 may operate at a maximum rate in response to a maximum activation of the switch 104. The motor 106 may operate at a lower rate in response to a less than maximum activation of the switch 104.

The motor 106 may produce rotary motion. The rotary motion delivered by the motor 106 may be delivered through a shaft 116. The shaft 116 may rotate around a shaft axis 126. In some embodiments, the reciprocating treatment device 100 may include a linkage to convert the rotary motion of the motor 106 into reciprocating motion. An embodiment of a linkage is shown in greater detail in relation to FIGS. 3A, 3B and 8-10 below.

In an alternative embodiment, the motor 106 may produce reciprocating motion. For example, the motor 106 may include a reciprocating pneumatic cylinder that reciprocates in response to an input of compressed air.

The actuated output 108, in some embodiments, reciprocates in response to an input from the motor 106. For example, the motor 106 may produce rotary motion. A gearbox may be connected to the motor 106 to convert the rotary motion to reciprocating motion. The gearbox may be connected to the actuated output 108. An embodiment of the gearbox is shown in greater detail in relation to FIGS. 4 and 8-10 below.

In some embodiments, the actuated output 108 reciprocates at a rate of approximately 65 Hz. The actuated output 108, in some embodiments, reciprocates at a rate over 50 Hz. The reciprocating treatment device 100, in some embodiments, provides reciprocation at a rate ranging between 50 Hz and 80 Hz. In some embodiments, the actuated output 108 has a maximum articulation rate of between 50 Hz and 80 Hz. In another embodiment, the actuated output 108 has an articulation rate of between 30 Hz and 80 Hz. In certain embodiments, the actuated output 108 has an articulation rate of approximately 37 Hz. In one embodiment, the actuated output 108 has an articulation rate of approximately 60 Hz. In a preferred embodiment, the actuated output 108 articulates or reciprocates at a frequency of between about 15 Hz and about 100 Hz. In a more preferred embodiment, the actuated output 108 articulates or reciprocates at a frequency of between about 25 Hz and about 48 Hz. In the most preferred embodiment, the actuated output 108 articulates or reciprocates at a frequency of between about 33 Hz and about 42 Hz. Any chosen range within the specified ranges is within the scope of the present invention.

The actuated output 108 may move through a predetermined range of reciprocation. For example, the actuated output 108 may be configured to have an amplitude of one half inch. In another embodiment, the actuated output 108 may be configured to have an amplitude of one quarter inch. As will be appreciated by one skilled in the art, the actuated output 108 may be configured to have any amplitude deemed therapeutically beneficial.

In some embodiments, the actuated output 108 may be adjustable through a variable range of reciprocation. For example, the reciprocating treatment device 100 may include an input to adjust the reciprocation amplitude from one quarter of an inch through a range of up to one inch. In a preferred embodiment, the actuated output 108 moves through an amplitude of between about 0.15 inches and about 1.0 inches. In a more preferred embodiment, the actuated output 108 articulates or reciprocates at a frequency of between about 0.23 inches and about 0.70 inches. In the most preferred embodiment, the actuated output 108 articulates or reciprocates at a frequency of between about 0.35 inches and about 0.65 inches. Any chosen range within the specified ranges is within the scope of the present invention.

It will be appreciated that the device operates most effectively within the combined frequency and amplitude ranges. When developing the invention, the inventor determined that if the frequency and amplitude are above the ranges set forth above the device can cause pain and below the ranges the device is ineffective and does not provide effective therapeutic relief or massage. Only when the device operates within the disclosed combination of frequency and amplitude ranges does it provide efficient and therapeutically beneficial treatment to the muscles targeted by the device.

In certain embodiments, the reciprocating treatment device 100 includes one or more components to regulate the articulation rate of the actuated output 108 in response to varying levels of power provided at the power input 102. For example, the reciprocating treatment device 100 may include a voltage regulator (not shown) to provide a substantially constant voltage to the motor 106 over a range of input voltages. In another embodiment, the current provided to the motor 106 may be regulated. In some embodiments, operation of the reciprocating treatment device 100 may be restricted in response to an input voltage being below a preset value.

In some embodiments, the actuated output 108 includes a connector 110 for connection of an attachment. In some embodiments, the actuated output 108 includes a securing mechanism 112 for securing an attachment in the connection socket 110. The connector 110 may be any type of structure capable of retaining an attachment, such as a socket with a latch, a threaded connector, or the like.

For example, the securing mechanism 112 may include a biased structure, such as a spring, to bias the securing mechanism 112 toward a locked position. In the locked position, the securing mechanism 112 may restrict removal of an attachment. The biased structure may be articulated by a user to move the securing mechanism 112 toward an unlocked position. In the unlocked position, the securing mechanism 112 may allow removal of an attachment.

In some embodiments, the securing mechanism 112 includes a keyway to interact with a key on an attachment. The keyway may be selectively opened and closed by articulation of the securing mechanism 112. Removal of an attachment may be restricted in response to the keyway being closed.

Figure 9:
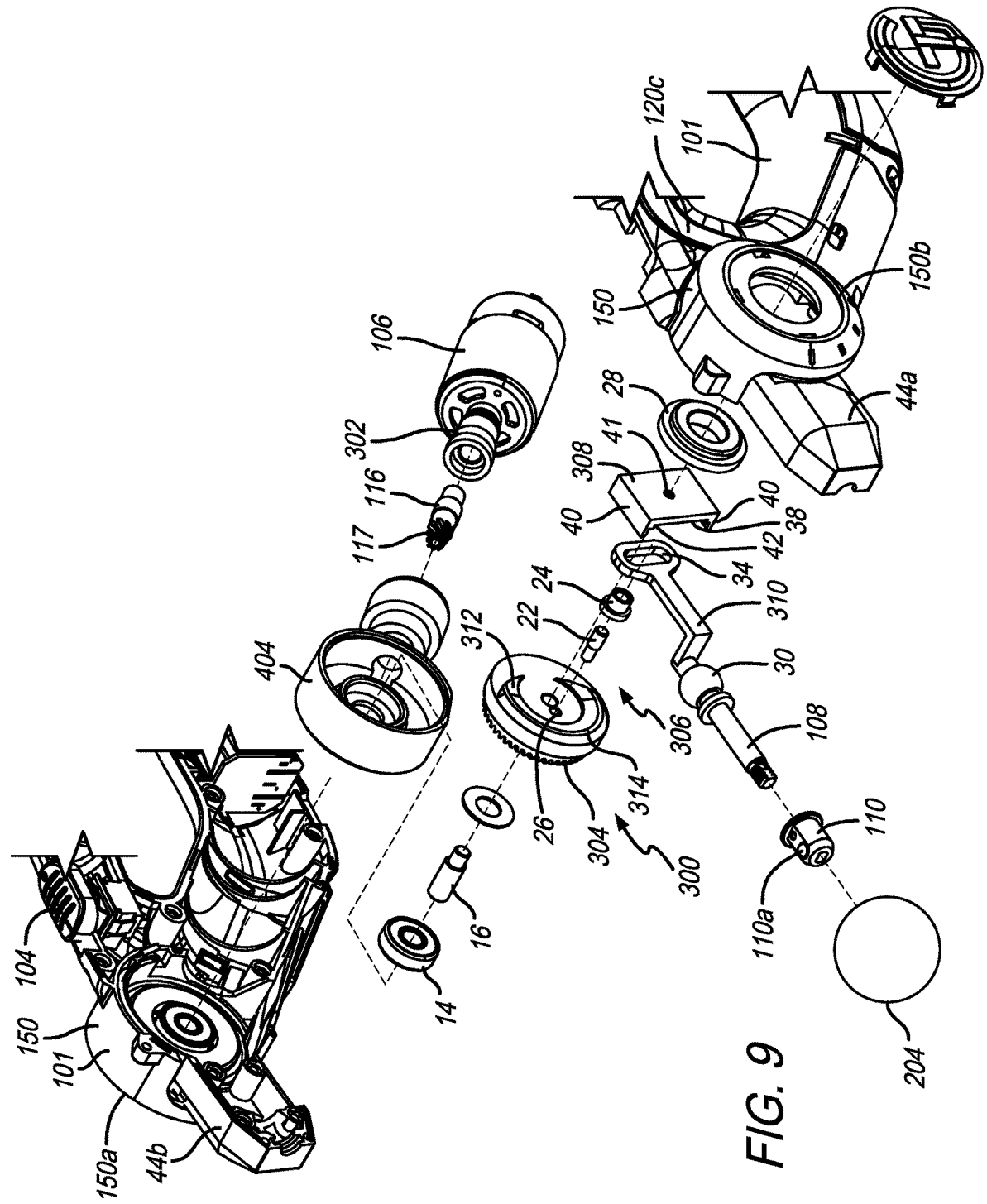
FIG. 9 is an exploded perspective view of a portion of the reciprocating treatment device of FIG. 7.

As shown in FIG. 9, in another embodiment, the connector 110 can be a male connector and can include at least one (and preferably two) outwardly biased ball bearings 110a that mate with the treatment structure 204.

In certain embodiments, the actuated output 108 reciprocates along a linear or substantially linear path. The path traveled by the actuated output 108 defines a reciprocation axis 124. In certain embodiments, the reciprocation axis 124 runs through the geometric center of one or more components of the actuated output 108.

The actuated output 108, in some embodiments, includes a safety extension 128 between a portion of the housing 101 and a protruding portion, such as the connection mechanism 112. The safety extension 128 provides a region of the actuated output 108 with a substantially constant cross-sectional profile. The safety extension 128 reduces the risk of pinching a body part, such as a finger, as the actuated output 108 actuates. The safety extension 128 may be defined as the region of the actuated output 108 between any non-reciprocating component, such as the housing 101, and any component of the actuated output 108 that has a relatively large or extending cross section, such as the connection mechanism. In one embodiment, the length of the safety extension 128 along the reciprocation axis 124, when measured when the actuated output 108 is fully retracted, is larger than the width of any of an average user's fingers. In some embodiments, the length of the safety extension 128 along the reciprocation axis 124, when measured when the actuated output 108 is fully retracted, is at least 18 millimeters.

In some embodiments, the motor 106 is connected to the housing 101 such that the shaft rotation axis 126 is parallel to a plane defined by the handle axis 122 and the reciprocation axis 124. In one embodiment, the motor 106 is connected to the housing 101 such that the shaft rotation axis 126 is coplanar with a plane defined by the handle axis 122 and the reciprocation axis 124.

Figure 2:
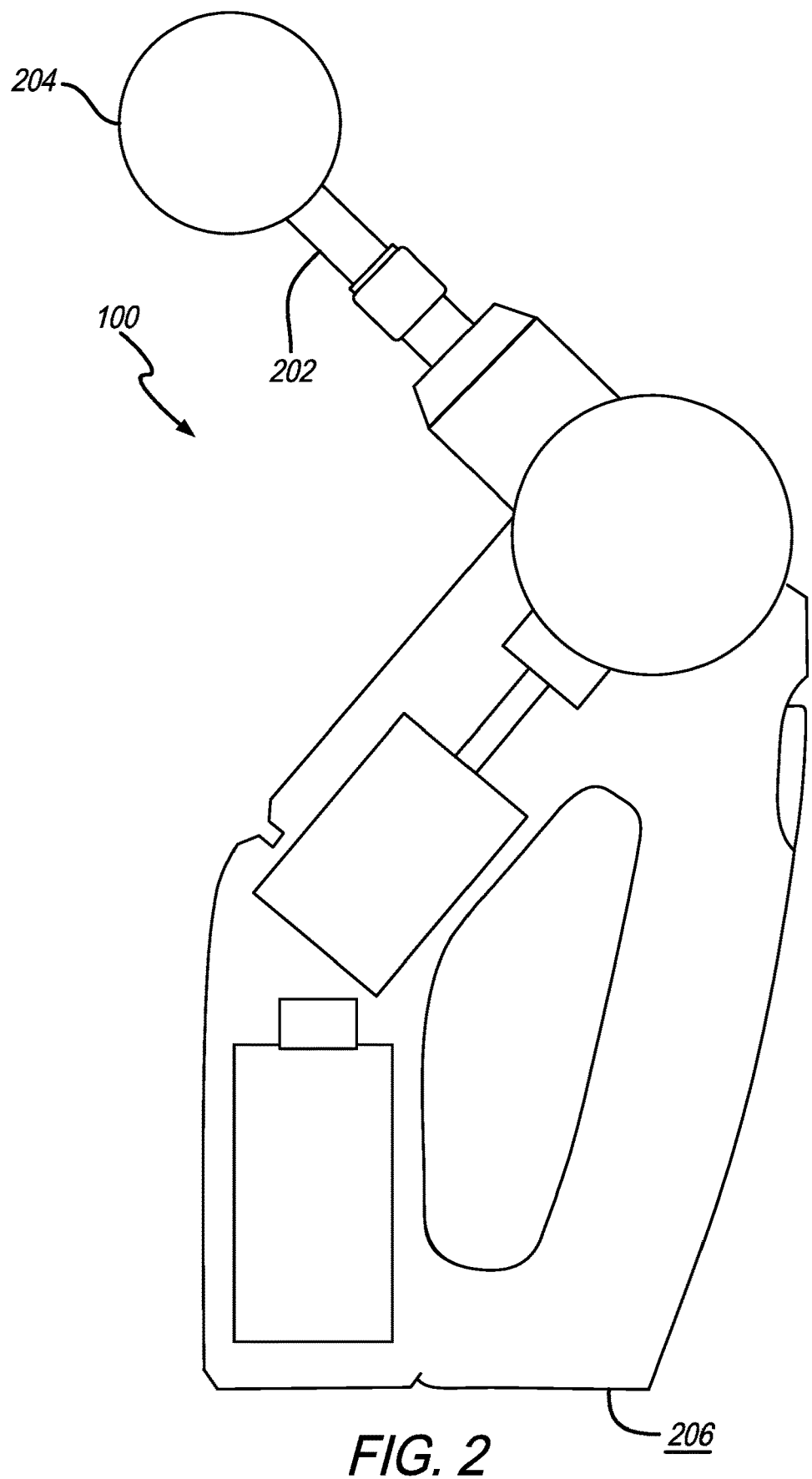
FIG. 2 depicts a side view of one embodiment of the reciprocating treatment device of FIG. 1.

FIG. 2 depicts a side view of one embodiment of the reciprocating treatment device 100 of FIG. 1. The reciprocating treatment device 100 includes an attachment 202, a treatment structure 204, and a rest surface 206. The reciprocating treatment device 100, in one embodiment, generates reciprocating motion at the treatment structure 204 for treating a patient.

The attachment 202 may be an interchangeable, user selectable component that is connectable to the actuated output 108. The attachment 202 may include a treatment structure 204 designed to interact with a patient.

The rest surface 206 is a surface disposed on the housing 101. The rest surface 206 is configured such that when the reciprocating treatment device 100 has the rest surface 206 placed on a flat, horizontal surface, the reciprocating treatment device 100 is capable of resting in that position without application of an external force. In other words, when resting as described above, a line drawn downward from a center of gravity of the reciprocating treatment device 100 passes through the rest surface 206. As used in this paragraph, "downward" refers to a direction in which gravity applies a force to objects having mass.

FIGS. 3A, 3B and 8-11E depict views of embodiments of the actuation components 300 for the reciprocating treatment device 100. The actuation components 300 generally include the motor 106, a compliant shaft damper 302, a shaft 116 with a shaft gear 117 thereon, a gear member 304, an eccentric interface 306, a reciprocator interface 308, a reciprocator shaft 310, and an actuated output 108. The motor 106, the shaft 116, and the actuated output 108 are similar to like-numbered components described above in relation to FIG. 1. The actuation components 300 create motion that is delivered at the actuated output 108.

In one embodiment, rotary motion is delivered from the motor 106 via the shaft 116 and gear 107. In certain embodiments, the motor 106 is connected to other components of the actuation components 300 by a compliant shaft damper 302. The compliant shaft damper 302 comprises a compliant material configured to absorb vibration generated by the actuation components 300. The compliant shaft damper 302 may transmit rotary motion generated by the motor 106 while deforming under vibration loads, thus absorbing or partially absorbing and reducing vibration in the reciprocating treatment device 100.

The compliant shaft damper 302 may include any material capable of absorbing vibration. In some embodiments, the compliant shaft damper 302 includes a polymer. For example, the compliant shaft damper 302 may include a flexible polymer. In one example, the compliant shaft damper 302 includes polyurethane foam, thermoplastic elastomer ("TPE"), including but not limited to Styrenic block copolymers (TPE-s), Polyolefin blends (TPE-o), Elastomeric alloys (TPE-v or TPV), Thermoplastic polyurethanes (TPU), Thermoplastic copolyester, or Thermoplastic polyamide. In another example, the compliant shaft damper 302 may include polyvinyl chloride (PVC), low durometer PVC, or a urethane.

The gear member 304, in one embodiment, receives rotary motion generated by the motor 106. In some embodiments, the gear member 304 rotates in response to rotation of the motor 106. In one embodiment, the gear member 304 rotates around a rotation axis 316 that is perpendicular to a shaft rotation axis 126. For example, the gear member 304 may be part of a bevel gear, a spiral bevel gear, or a hypoid gear. Such gears may have the effect of rotating an axis of rotation by 90 degrees.

In some embodiments, the gear member 304 includes an eccentric interface 306. The eccentric interface 306 is disposed on a surface of the gear member 304 such that it or its center is at a location not on the gear rotation axis 316. In other words, if the gear member 304 is round, the eccentric interface 306 is not disposed at the center of the gear member 304.

In response to rotation of the gear member 304 and subsequent motion of the eccentric interface 306, the reciprocator interface 308 restricts linear motion of the eccentric interface 306 relative to the reciprocator interface 308 to a direction perpendicular to both the reciprocation axis 124 and the gear rotation axis 316. In other words, the eccentric interface 306 is free to slide side-to-side within the reciprocator interface 308 as the gear member 304 rotates. Note that the in addition to sliding relative to the reciprocator interface 308, the eccentric interface 306 may rotate.

As shown in FIG. 9, in a preferred embodiment, the eccentric interface 306 includes a pin 22 and sleeve 24. The pin 22 is received in an off-center opening 26 defined in or through the gear member 304. The sleeve 24 is received in an elongated opening 34 that is defined in an end or head 36 of the reciprocator shaft 310.

The eccentric interface 306, in one embodiment, interfaces with a reciprocator interface or containment member 308. The containment member 308 contains the head 36 of the reciprocator shaft 310 and defines a reciprocation space 38 in which the head 36 of the reciprocator shaft 310 and the eccentric interface components 306 can reciprocate. The containment member 308 includes legs 40 that each include an interior surface that defines a step 42 therein. The larger dimension between the legs defines a space for the head 36 to reciprocate and the smaller dimension between the legs defines a space for the sleeve to reciprocate. In a preferred embodiment, the reciprocator shaft 310 is L-shaped or includes an arm portion so that it connects to the actuated output or shaft 108 along the reciprocation axis.

In some embodiments, the effect of the interaction between the eccentric interface 306 and the reciprocator interface 308 is to convert rotary motion at the gear member 304 to reciprocating, linear motion at the reciprocator shaft 310. The reciprocator shaft 310 transmits reciprocating, linear motion to the actuated output 108.

Figure 3A:
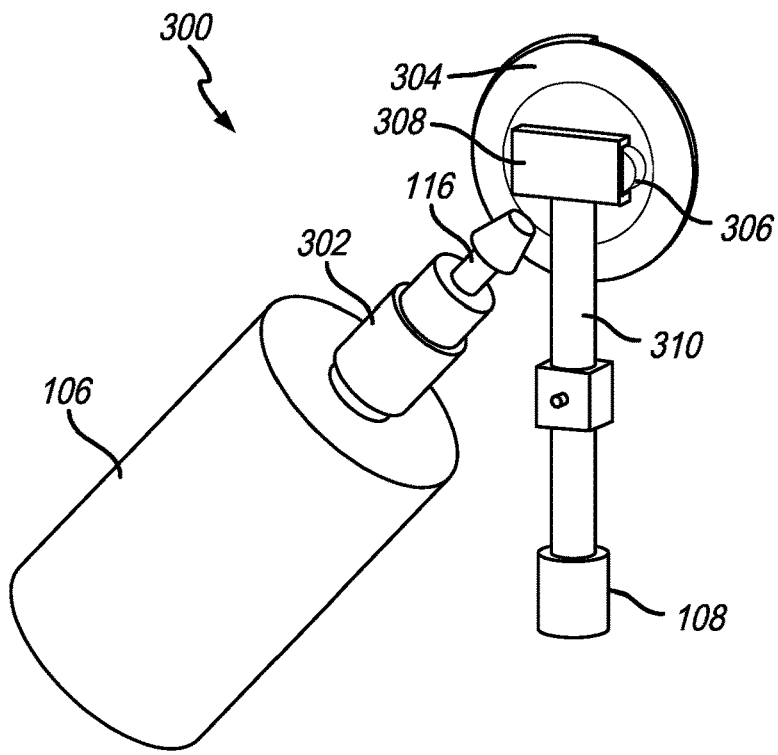
FIGS. 3A and 3B depict perspective views of embodiments of actuation components the reciprocating treatment device of FIG. 1.
Figure 3B:
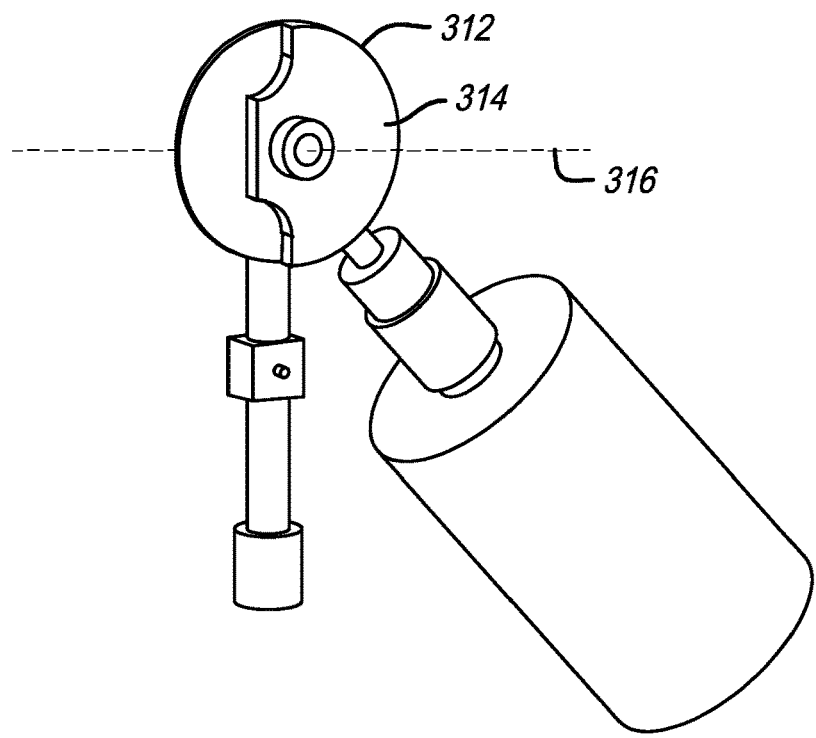
Figure 4:
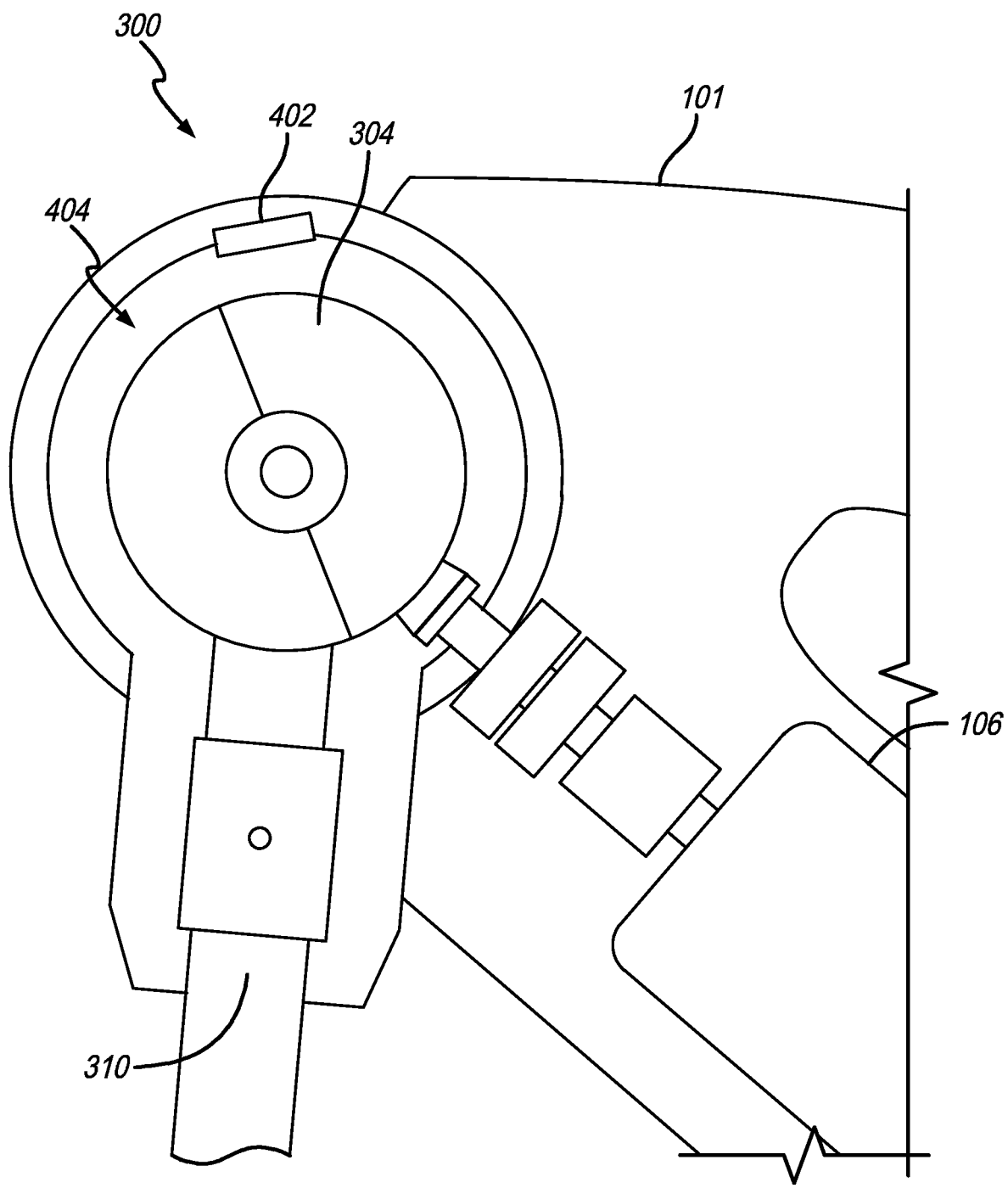
FIG. 4 depicts a side view of one embodiment of actuation components of the reciprocating treatment device of FIG. 1.

As shown in FIGS. 3B and 9, in one embodiment, the gear member 304 includes a counterweight 312. The counterweight 312 is configured to oppose inertial forces generated by the reciprocating motion of the actuated output 108. The counterweight 312 may be positioned on the gear member 304 such that its center of mass 314 is not located along the gear rotation axis 316. In certain embodiments, a first direction from the gear rotation axis 316 to the center of mass 314 of the counterweight 312 may be the opposite direction from a second direction from the gear rotation axis 316 to the center of the eccentric interface 306. Preferably, the counterweight 312 is located on one side of the gear member 304 and the gear teeth are located on the opposite side. In another embodiment, the gear and counterweight can be separate parts.

In some embodiments, as the reciprocating treatment device 100 operates, the counterweight 312 applies at least a component of force in the opposite direction to a reaction force applied to the eccentric interface 306 by the reciprocator interface 308. In other words, the counterweight 312 may serve to counteract an inertial force generated by reciprocating components and reduce vibration caused by reciprocal motion of the actuated output 108.

In some embodiments, the counterweight 312 may be sized to match reciprocating components of the reciprocating treatment device 100. For example, the counterweight 312 may have a mass similar to reciprocating components, including, for example, the reciprocator shaft 310, the actuated output 108, and an attachment 202. In another embodiment, the counterweight has a mass between 45 grams and 55 grams.

Figure 11A:
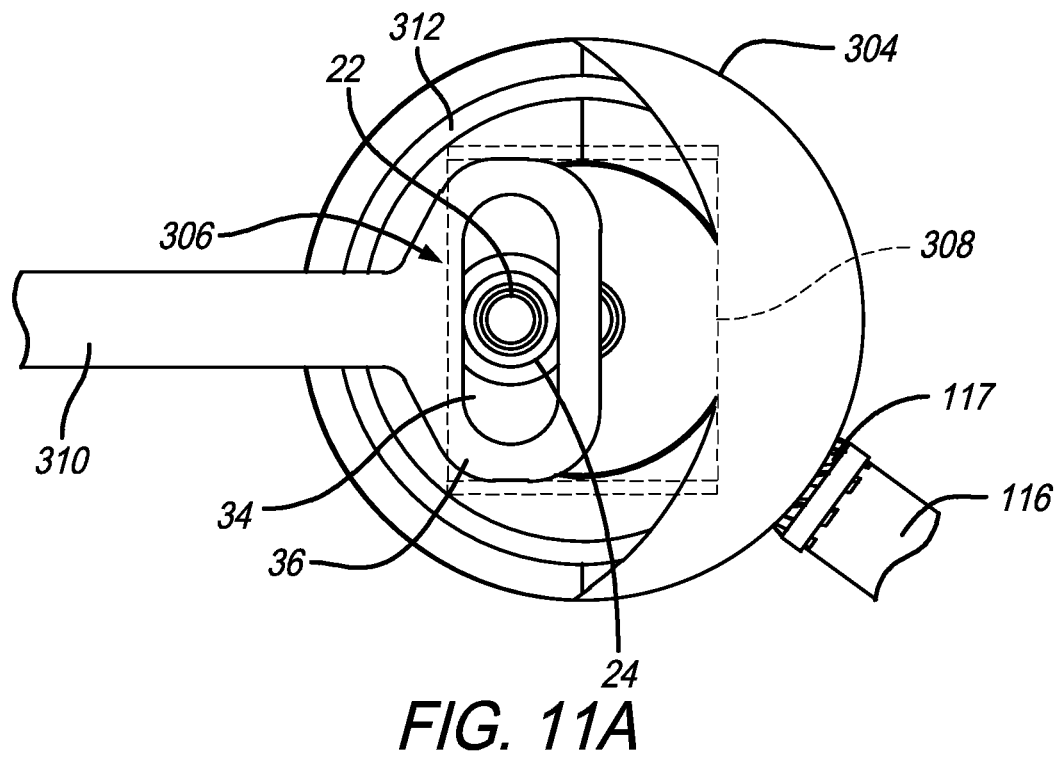
FIG. 11A depicts the reciprocator shaft in the extended position.
Figure 11B:
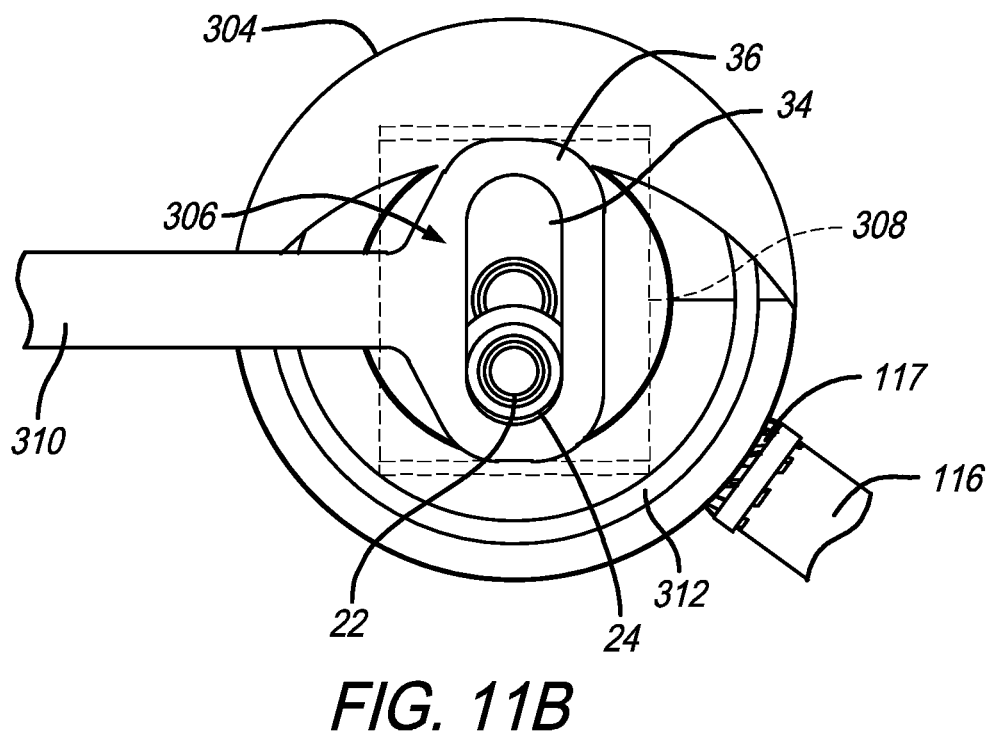
FIG. 11B depicts the reciprocator shaft between the extended and retracted positions.
Figure 11C:
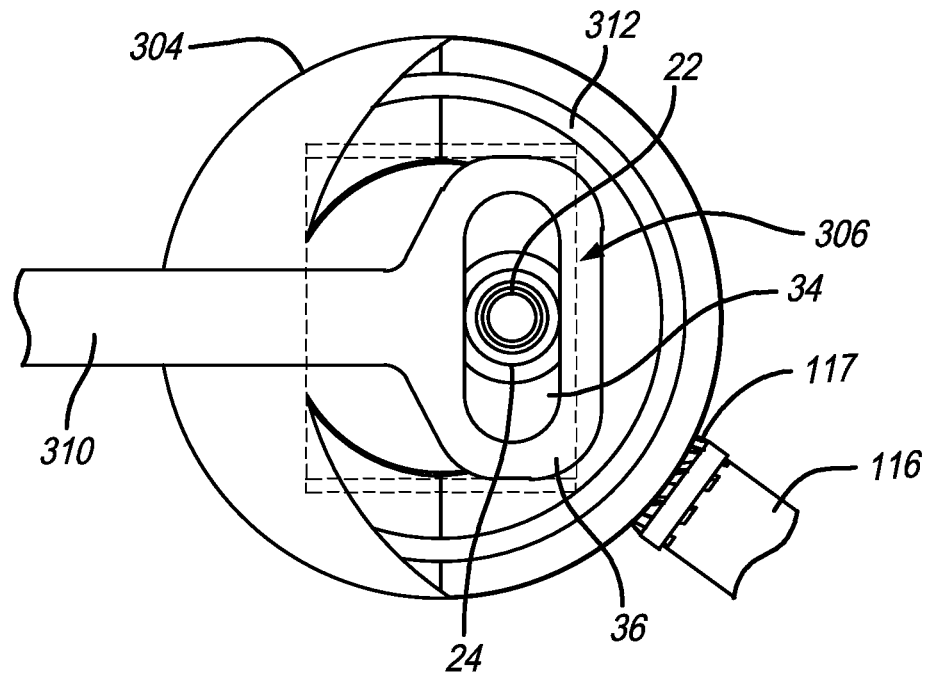
FIG. 11C depicts the reciprocator shaft in the retracted position.
Figure 11D:
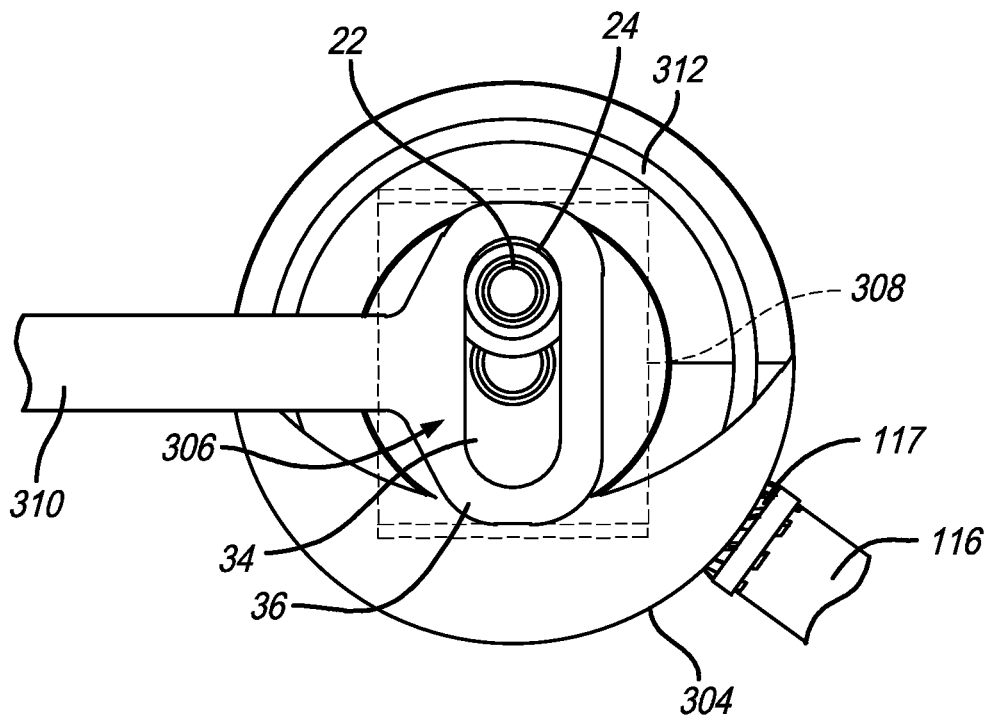
FIG. 11D depicts the reciprocator shaft between the extended and retracted positions.
Figure 11E:
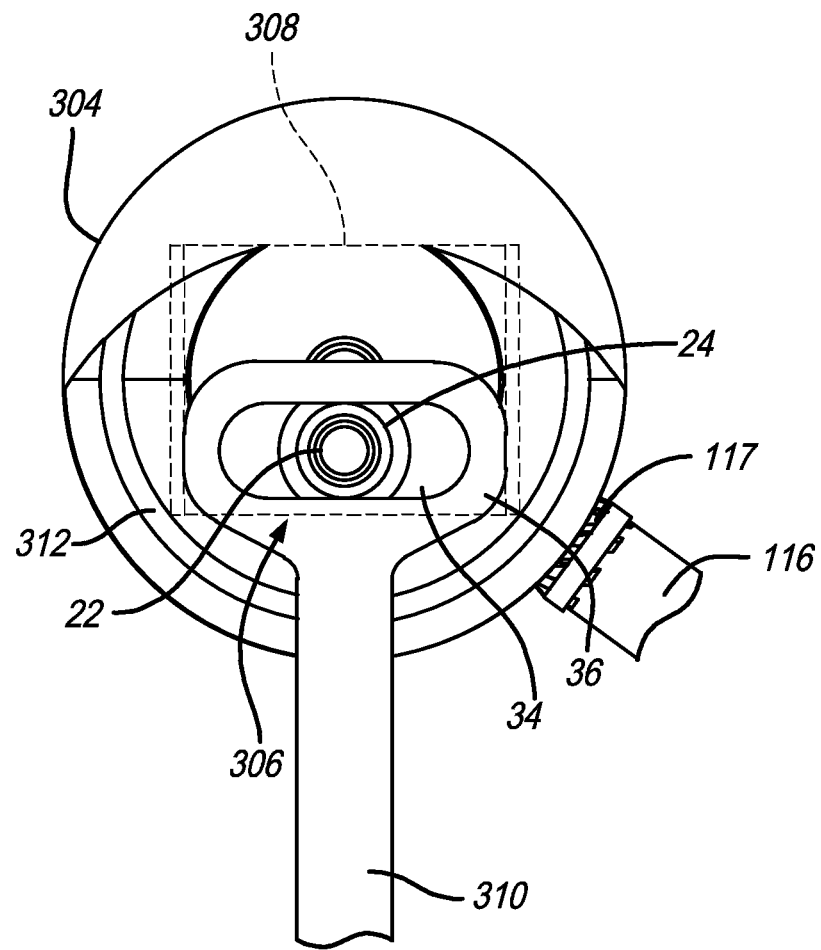
FIG. 11E depicts the reciprocator shaft in the extended position, but after being rotated relative to FIGS. 11A-11D.

FIG. 11A shows the reciprocator shaft 310 in the extended position and FIG. 11C shows the reciprocator shaft 310 in the retracted position. FIGS. 11B and 11D show the reciprocator shaft in between the retracted and extended positions. Note how the pin 22 and sleeve 24 (eccentric interface) move within elongated opening 34 and the containment member 308 keeps the head 36 of the reciprocator shaft 310 moving linearly. FIG. 11E shows the reciprocator shaft 310 in the extended position, but after the rotation assembly 47 has been rotated, as discussed below.

Figure 10:
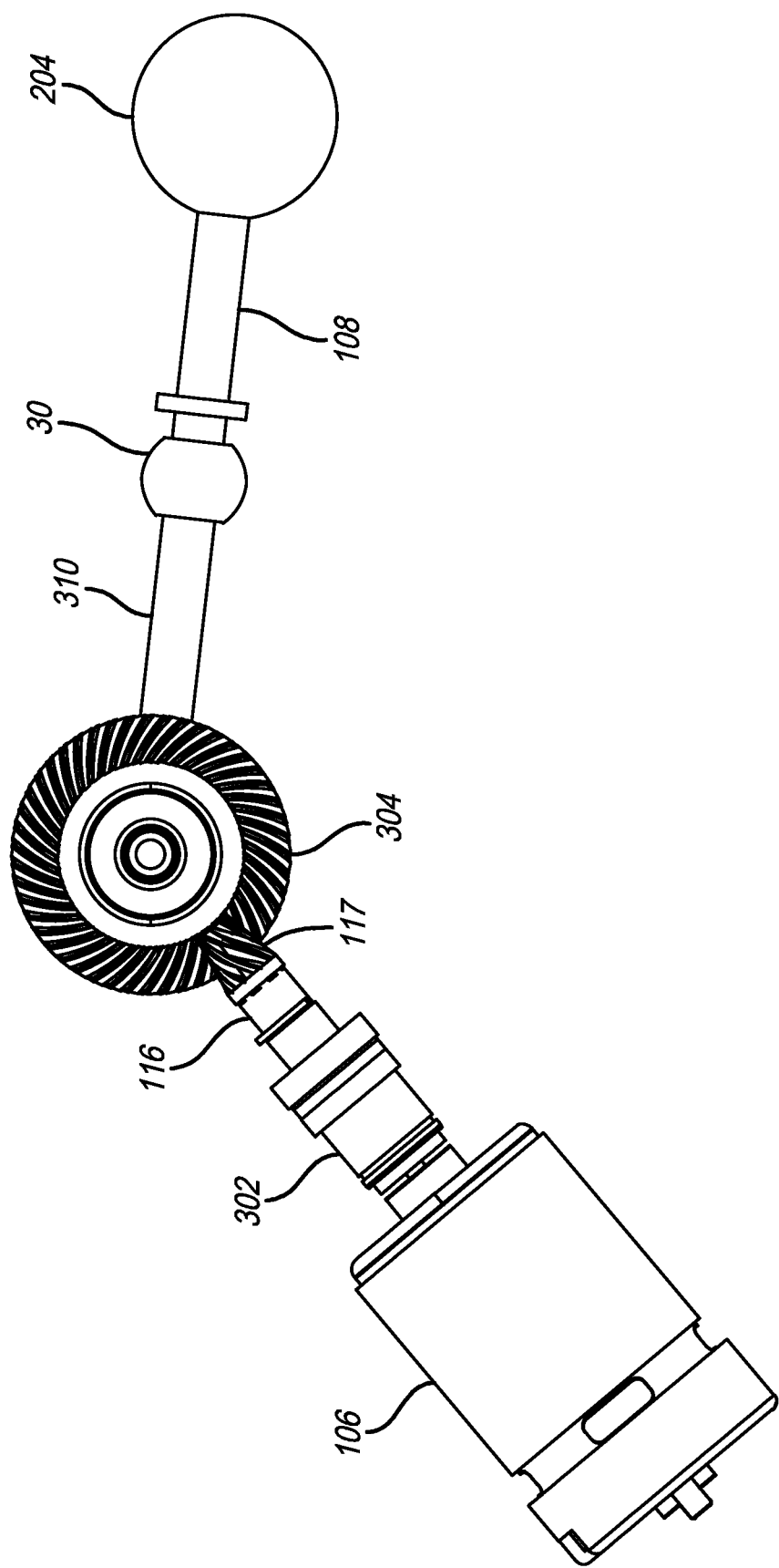
FIG. 10 is a side elevational view of the motor and actuation components of the reciprocating treatment device of FIG. 7.

As shown in FIGS. 8-10, the actuation components 300 include a guide member 30 that includes a central opening through which the reciprocator shaft 310 extends. The guide member 30 is housed in the rotation housing 44 and remains stationary as the reciprocator shaft moves therein. In a preferred embodiment, the actuation components 300 also include a pin or axle 16 on which the gear member 304 rotates a bearing 14 and a dampening ring 28 for damping the connection between the housing and the metal components.

FIGS. 4 and 8-11E depict embodiments of actuation components 300 of the reciprocating treatment device 100. The actuation components include the motor 106, the gear member 304, the reciprocator shaft 310, one or more compliant dampening blocks 402 and, a gearbox 404. The actuation components 300 provide reciprocating motion through the reciprocator shaft 310 and manage vibration transmitted to the housing 101.

The one or more compliant dampening blocks 402 manage vibration conducted from the actuation components 300 to the housing 101. The one or more compliant dampening blocks 402 may be disposed between the actuation components 300 and the housing 101.

The one or more compliant dampening blocks 402 may include any material capable of absorbing vibration. In some embodiments, the one or more compliant dampening blocks 402 include a polymer. For example, the one or more compliant dampening blocks 402 may include a flexible polymer. In one example, the one or more compliant dampening blocks 402 include polyurethane foam, thermoplastic elastomer ("TPE"), including but not limited to Styrenic block copolymers (TPE-s), Polyolefin blends (TPE-o), Elastomeric alloys (TPE-v or TPV), Thermoplastic polyurethanes (TPU), Thermoplastic copolyester, or Thermoplastic polyamide. In another example, the one or more compliant dampening blocks 402 may include polyvinyl chloride (PVC), low durometer PVC, or a urethane.

The gearbox 404, in one embodiment, includes the gear member 304 and the reciprocator 310. The gearbox 404 may provide mounting points for the gear member 304 and the reciprocator 310. The gearbox 404 may restrict the motion of the gear member 304 and the reciprocator to certain directions or rotational axes. The gearbox 404 may be mounted to the housing 101. In some embodiments, the gearbox 404 is separated from the housing 101 by the one or more compliant dampening blocks 402.

Figure 12:
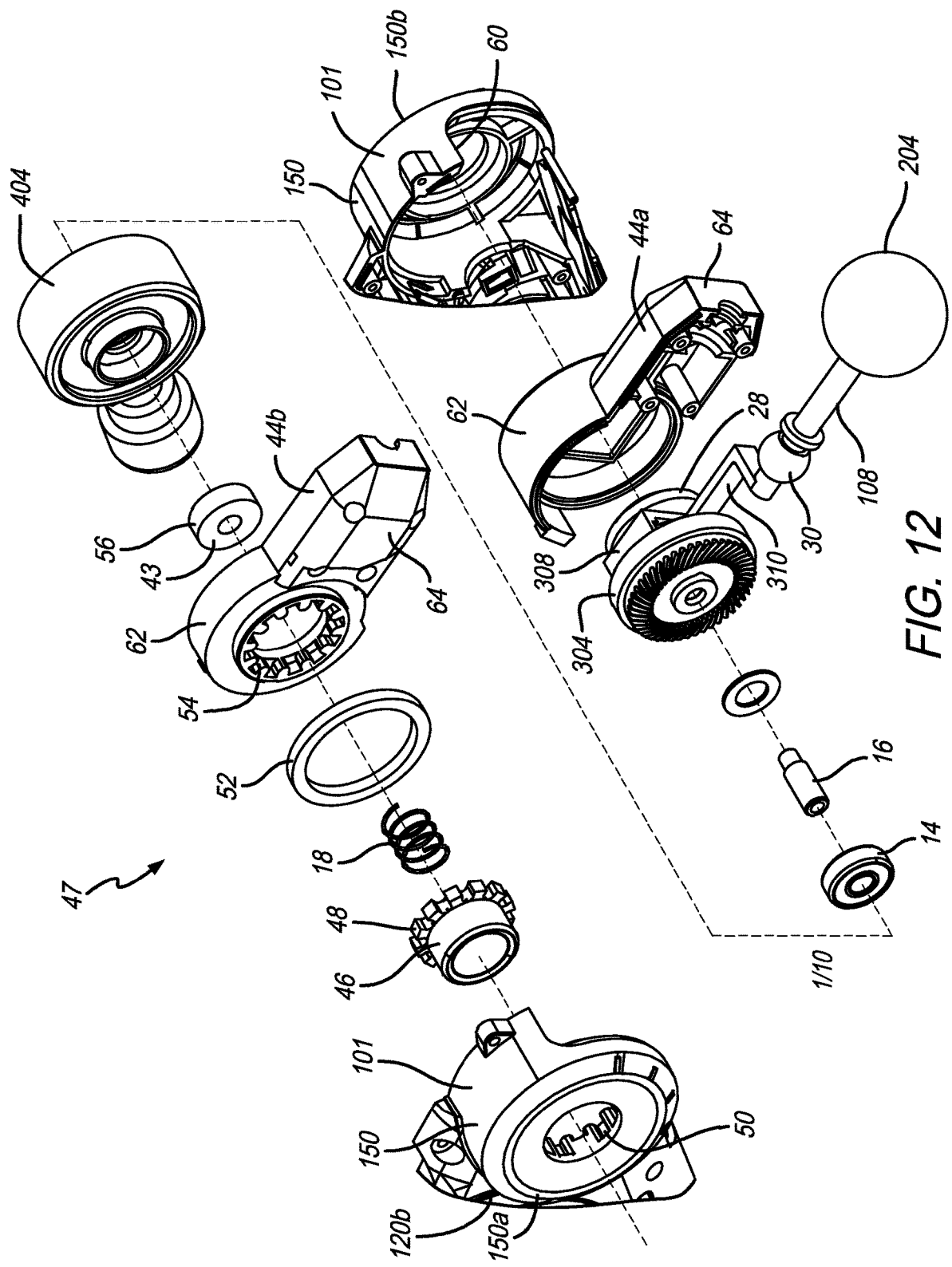
FIG. 12 is an exploded perspective view of the components associated with the rotation of the arm.
Figure 13:
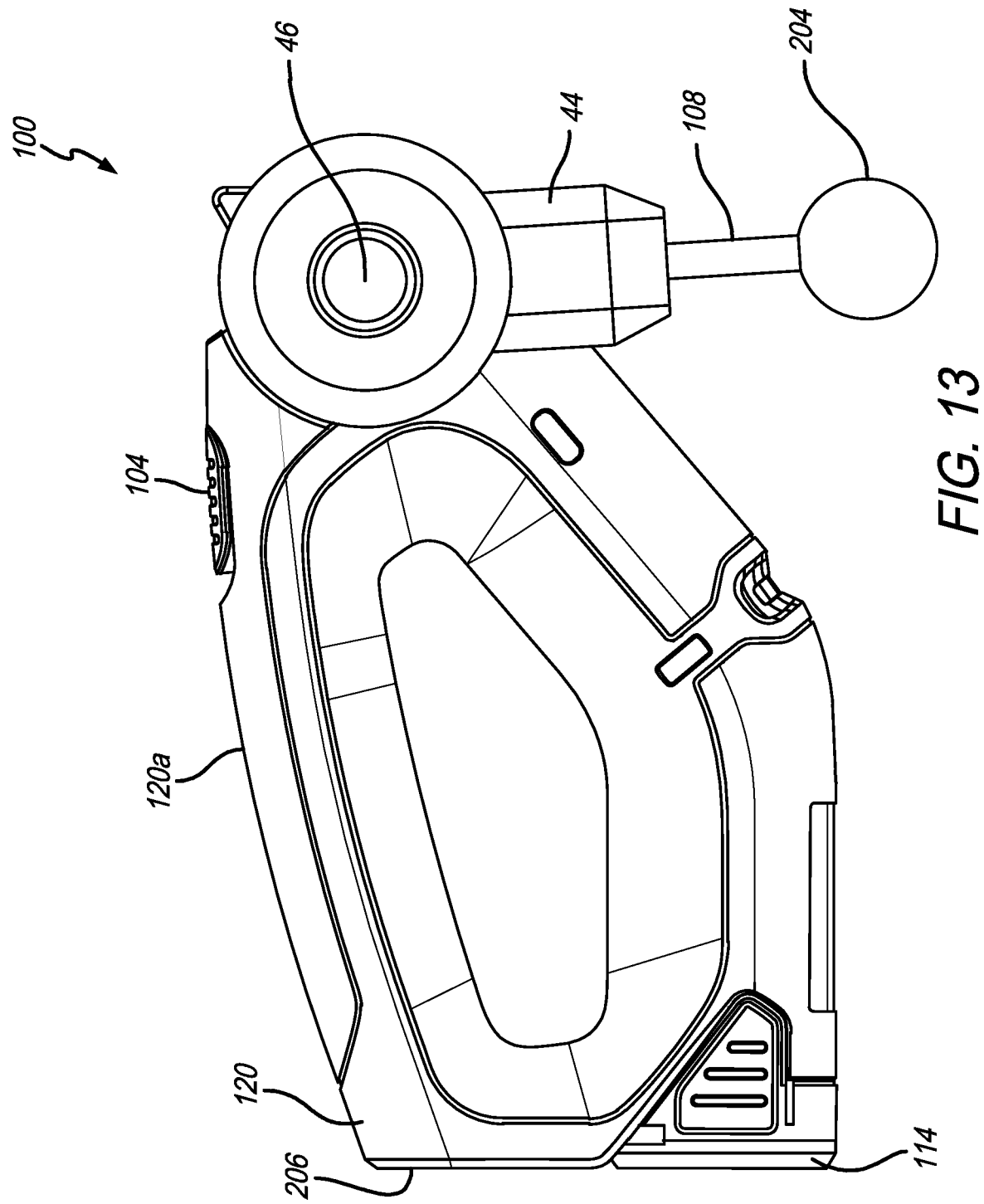
FIG. 13 is a side elevational view with the rotation housing and actuated output rotated to a vertical position (compare to the horizontal position in FIG. 7)

As is shown in FIGS. 11C and 12, in some embodiments, the actuated output 108 and associated components are rotatable relative to the housing 101. The actuated output 108 may rotate relative to the housing 101 around an output rotation axis. In certain embodiments, the output rotation axis is parallel to the gear rotation axis 316. In one embodiment, the output rotation axis is concomitant with the gear rotation axis 316. For example, the actuated output 108, the reciprocator 310, and the reciprocator interface 308 may be selectively rotatable around the gear rotation axis 316.

In one embodiment, rotation of the actuated output 108 may be selectively locked and unlocked by a user. For example, the user may unlock rotation of the actuated output 108, rotate the actuated output 108 to a desired position relative to the housing 101, lock rotation of the actuated output 108, and operate the reciprocating treatment device 100.

As shown in FIG. 12 in a preferred embodiment, the rotation assembly 47 includes the rotation housing 44 (which includes first and second rotation housing halves 44a and 44b), an articulation lock or a button 46 having teeth 48 thereon and a spring 18 that contacts seating surface 43. The gear member 304, reciprocator shaft 310, axle 16, a portion of the gear box 404, and bearing 14 are all housed in the rotation housing 44. The assembly also includes a gear box cover 56 and dampening ring 52. Button 46 is outwardly biased by spring 18 to a position where teeth 48 are engaged with teeth 50 defined in housing 101. The button 46 is movable between a first position where teeth 48 are engaged with teeth 50 and a second position where teeth 48 are engaged with teeth 54 in the second rotation housing half 44*b*. When the button 46 is in the first position, the rotation assembly 47 cannot rotate. When the button is pushed to the second position, the teeth 48 disengage from teeth 50 and engage the teeth 54 in the rotation housing 44, thereby allowing the entire rotation assembly 47 to rotate. The rotation housing 44 includes a main body portion 62 disposed in the housing and an arm portion 64 extending through the rotation space 60 and outside the housing. The arm portion 64 rotates within the rotation space 60 defined in the housing 101. It will be appreciated, that when rotation occurs, gear member 304 and gear box 404 do not rotate (compare FIGS. 11A-11D to FIG. 11E), but the containment member 308 together with the actuated output 108 do rotate. As shown in FIGS. 8, 9 and 12, the housing 101 includes a bulge portion 150 having a first bulge portion surface 150*a* positioned on a first side of a plane that bifurcates the housing 101 (referred to herein as the "housing plane") and a second bulge portion surface 150*b* positioned on a second side of the housing plane. The handle 120 includes a first handle side surface 120*b* positioned on the first side of the housing plane and a second handle side surface 120*c* positioned on the second side of the housing plane. The first bulge portion surface 150*a* is located further from the housing plane than the first handle side surface 120*b* and the second bulge portion surface 150*b* is located further from the housing plane than the second handle side surface 120*c*.

Figure 5:
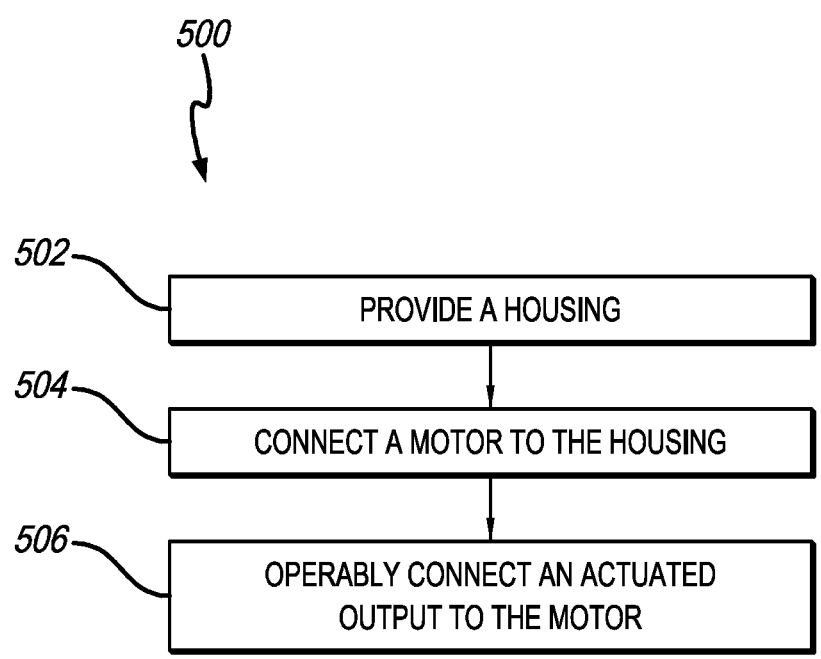
FIG. 5 depicts a flowchart diagram showing one embodiment of a method of manufacture of the reciprocating treatment device of FIG. 1.

FIG. 5 depicts a flowchart diagram showing one embodiment of a method of manufacture of the reciprocating treatment device of FIG. 1.

FIGS. 5 and 6 are flowchart diagrams depicting embodiments of a method 500 for manufacturing the reciprocating treatment device 100 of FIG. 1 and a method 600 of use of the reciprocating treatment device 100 of FIG. 1. The methods 500, 600 are, in certain embodiments, methods of use of the system and apparatus described herein, and will be discussed with reference to those figures. Nevertheless, the methods 500, 600 may also be conducted independently thereof and are not intended to be limited specifically to the specific embodiments discussed above with respect to those figures.

As shown in FIG. 5, a method of manufacture 500 for a reciprocating treatment device 100 is shown. In one embodiment of the method of manufacture 500, a housing 101 is provided 502. The housing 101 may include a handle 120 and the handle 120 may define a handle axis 122. A motor 106 is connected 504 to the housing 101. The motor 106 may provide rotary motion.

In some embodiments, an actuated output 108 is operably connected 506 to the motor 106. The actuated output 108 may reciprocate in response to activation of the motor 106. Reciprocation of the actuated output 108 may be along a reciprocation axis 124.

In some embodiments, the motor 106 includes a shaft 116. The shaft 116 may rotate around a shaft rotation axis 126. The shaft rotation axis 126 may be parallel to a plane in which the handle axis 122 and the reciprocation axis 124 are located.

As shown in FIG. 6, a method of use 600 for a reciprocating treatment device 100 is shown. In one embodiment of the method of use 600, a force is applied 602 to a body part by an actuated output 108 of the reciprocal treatment device 100. The reciprocal treatment device 100 may include a housing 101. The housing 101 may include a handle 120 disposed on the housing 101. The handle 120 may define a handle axis 122.

The reciprocal treatment device 100 may also include a motor 106 connected to the housing 101. An actuated output 108 may be operably connected to the motor 106. The actuated output 108 may be configured to reciprocate in response to activation of the motor 106. Reciprocation of the actuated output 108 may be along a reciprocation axis 124.

The motor 106 may include a shaft 116 having a shaft rotation axis 126. The shaft rotation axis 126 may be parallel to a plane in which the handle axis 122 and the reciprocation axis 124 are located.

FIGS. 14-27 show further embodiments of the present invention. Many of the components of the reciprocal treatment devices or percussive massage devices of FIGS. 14-27 are the same or similar as those discussed above with respect to reciprocal treatment device 100. Accordingly, the description hereinafter focuses on components that are different.

Figure 14:
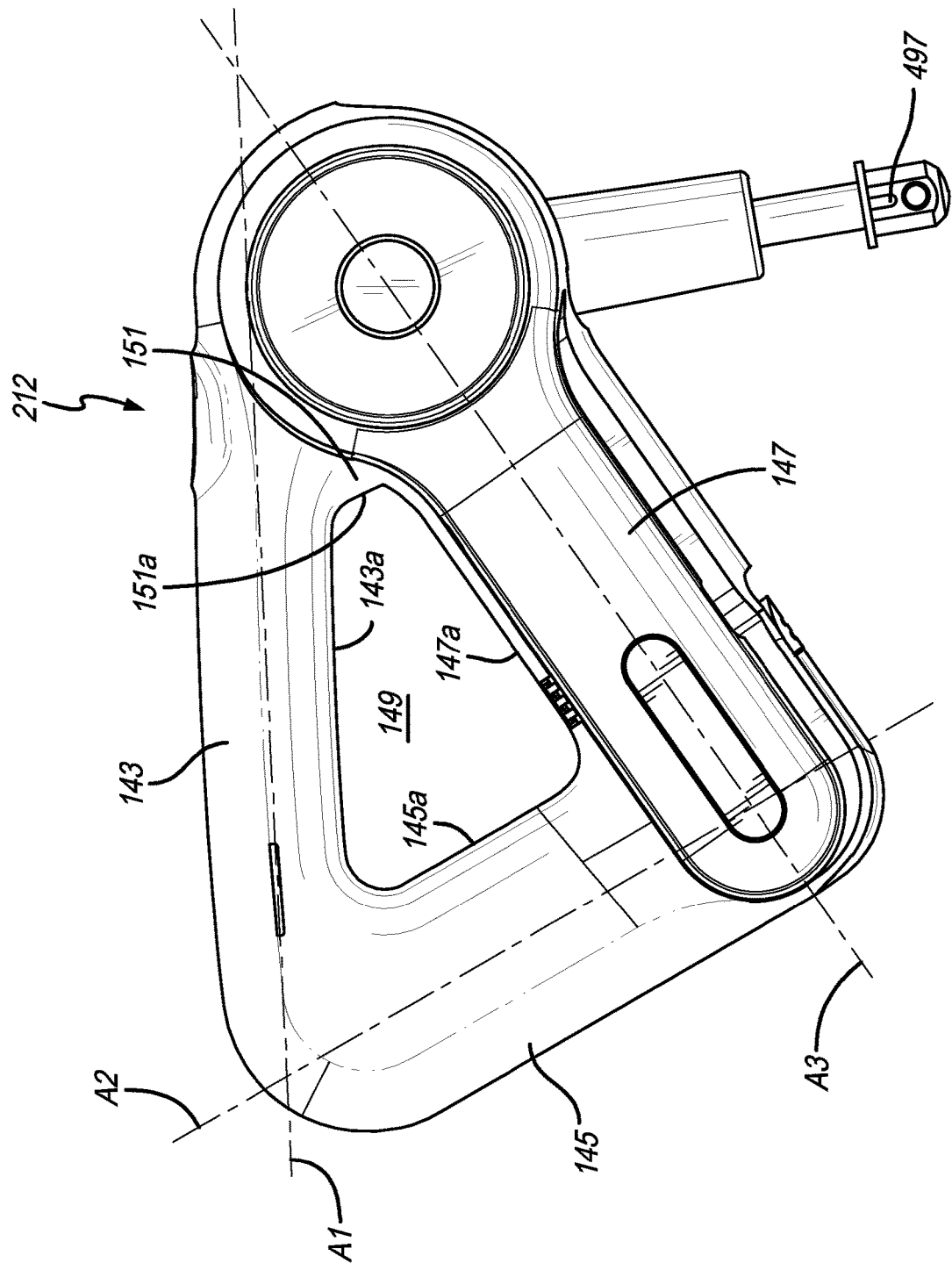
FIG. 14 is a side elevational view of a percussive massage device in accordance with a preferred embodiment of the present invention.
Figure 15:
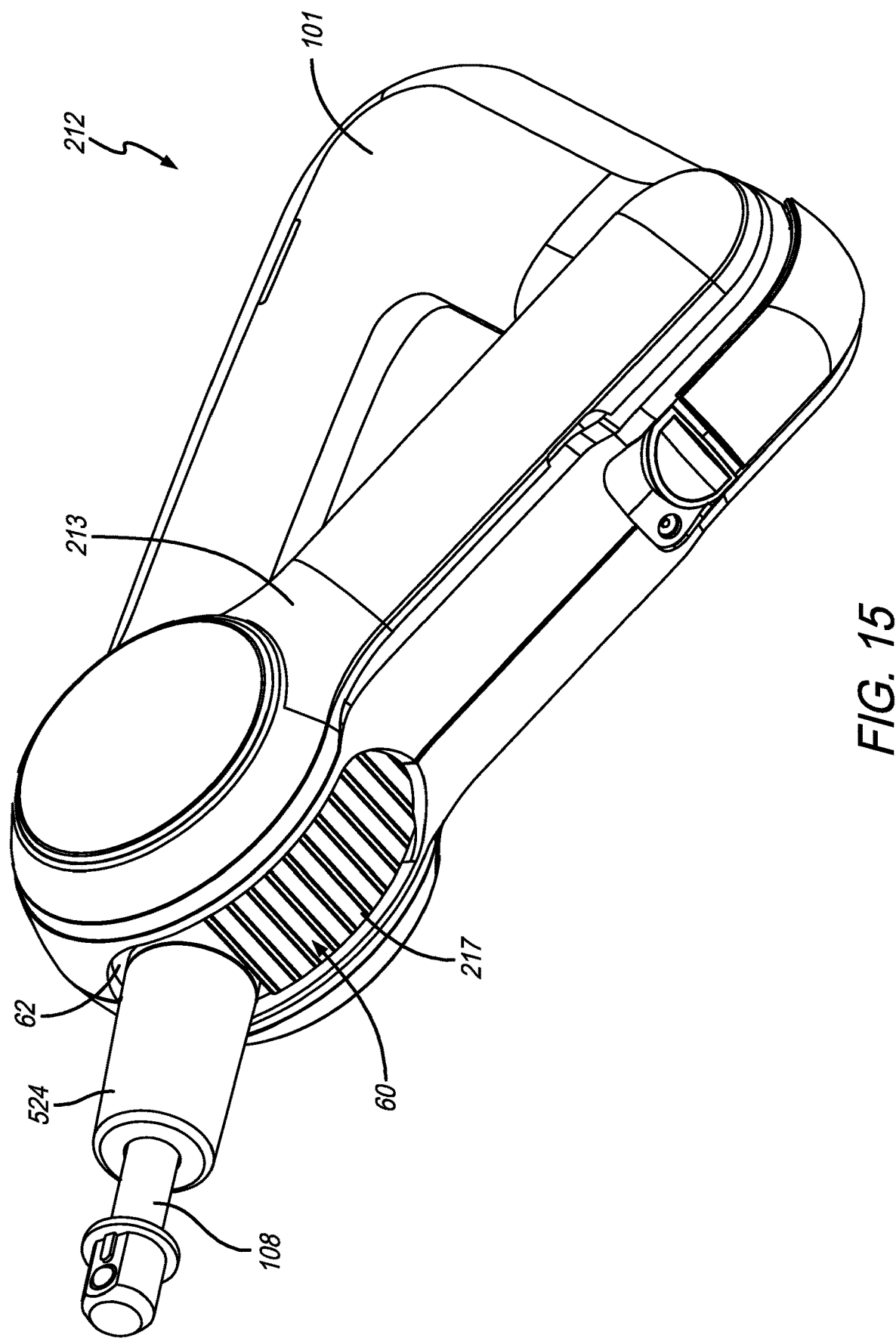
FIG. 15 is a perspective view of the percussive massage device.

FIGS. 14-23 show an embodiment of a percussive massage device 212 that includes a rechargeable battery (and replaceable or removable battery) 114. Device 212 is referred to commercially as the G3PRO. As shown in FIGS. 14-15, in a preferred embodiment, the percussive massage device 212 includes three handle portions (referred to herein as first handle portion 143, second handle portion 145 and third handle portion 147) that cooperate to define a central or handle opening 149. All of the handle portions are long enough that they are configured such that a person can grasp that particular handle portion to utilize the device. The ability to grasp the different handle portions allows a person (when using the device on their own body) to use the device on different body parts and from different angles, thus providing the ability to reach body parts, such as the back, that might not be possible without the three handle portions.

As shown in FIG. 14, the first handle portion 143 defines a first handle portion axis A1, the second handle portion 145 defines a second handle portion axis A2 and the third handle portion 147 defines a third handle portion axis A3 that cooperate to form a triangle. In a preferred embodiment, the battery 114 is housed in the second handle portion 145 and the motor 106 is housed in the third handle portion 147.

Figure 16:
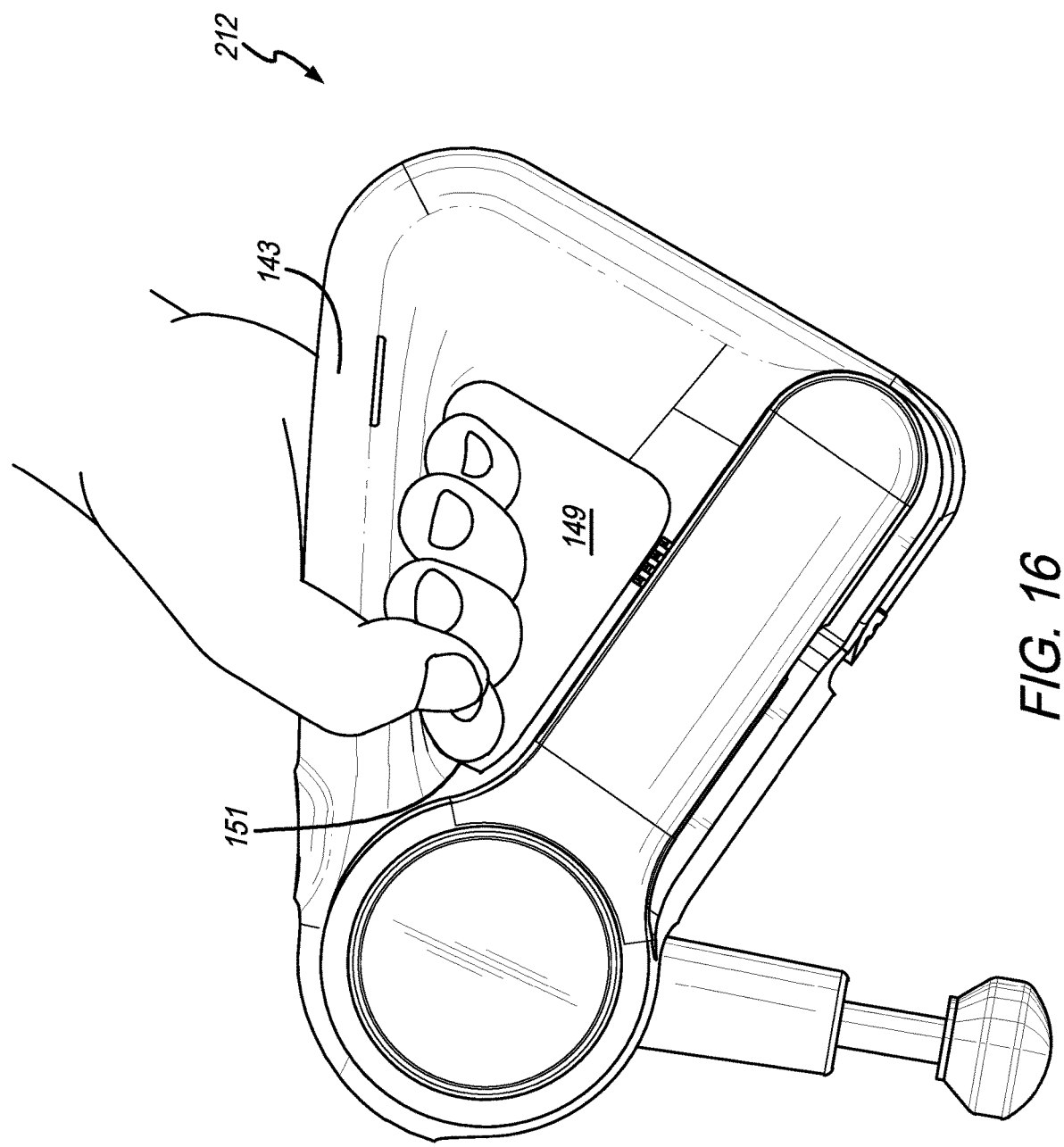
FIG. 16 is a side elevational view of the percussive massage device showing a user grasping the first handle portion.
Figure 17:
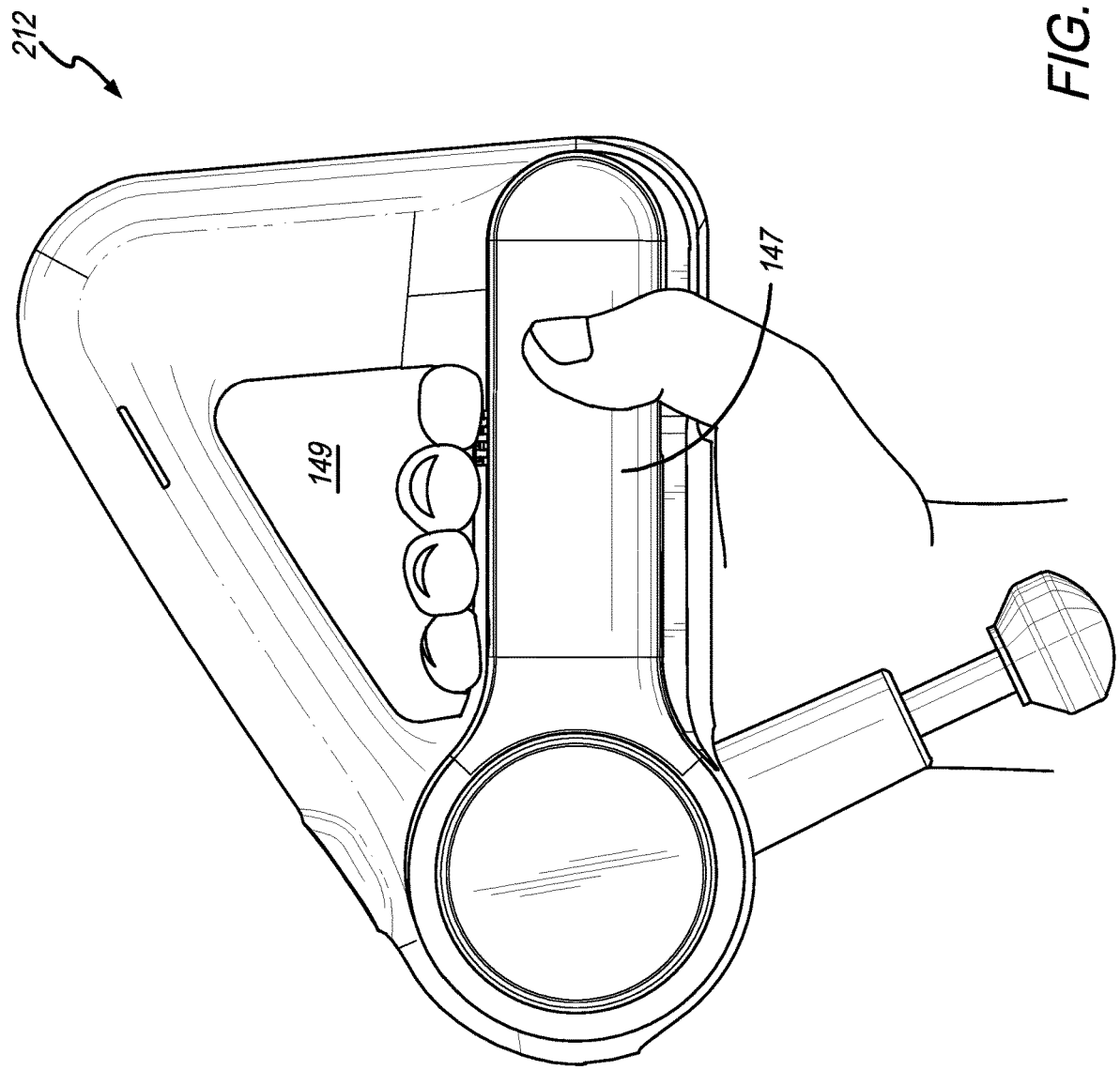
FIG. 17 is a side elevational view of the percussive massage device showing a user grasping the third handle portion.
Figure 18:
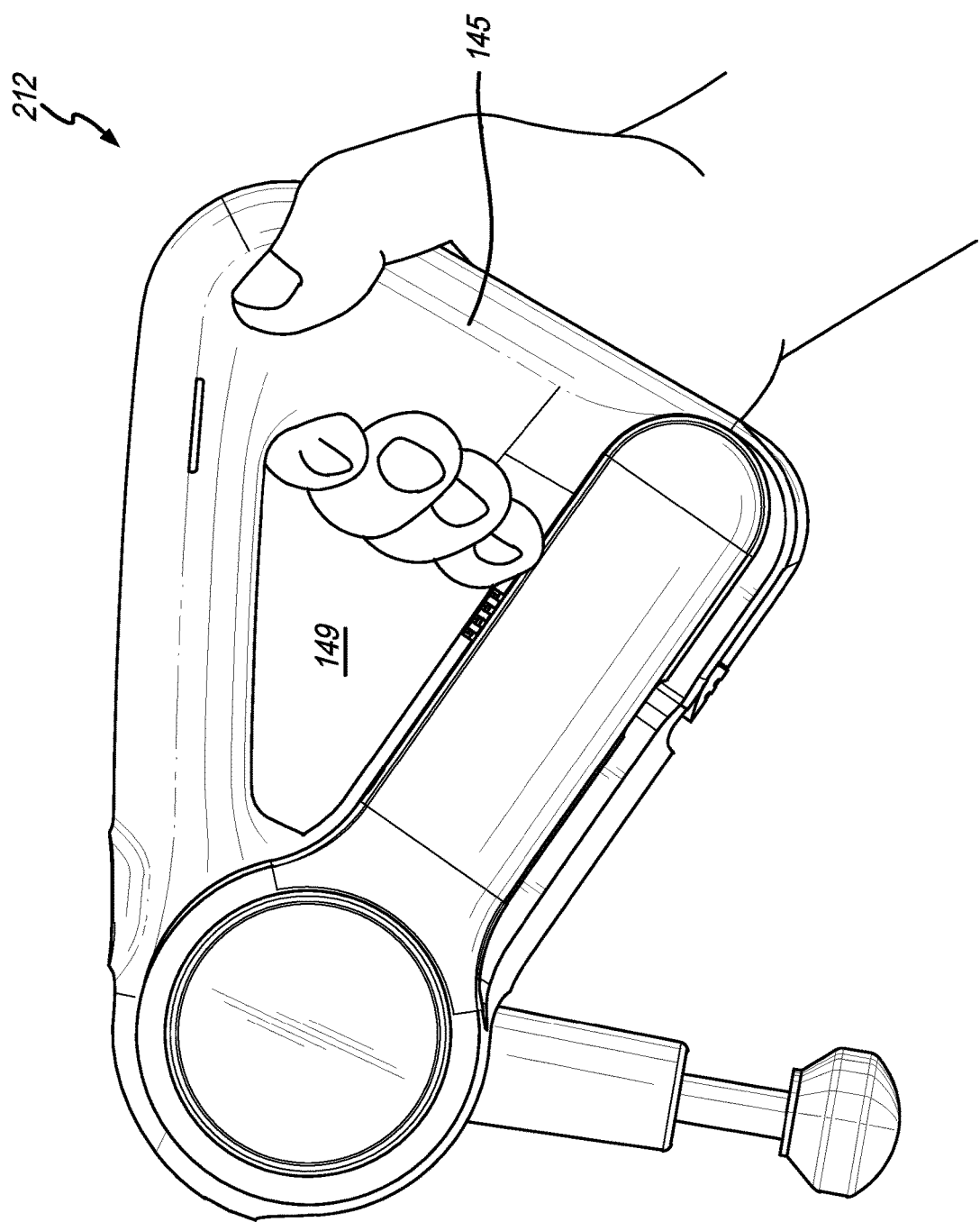
FIG. 18 is a side elevational view of the percussive massage device showing a user grasping the second handle portion.

FIGS. 16-18 show a user's hand grasping the various handle portions. The length of each of the first, second and third handle portions is long enough so that a person with a large hand can comfortably grasp each handle portion with at least three to four fingers extending through the handle opening, as shown in FIGS. 16-18. In a preferred embodiment, the first handle portion 143 has an interior edge 143*a*, the second handle portion 145 has an interior edge 145*a* and the third handle portion 147 has an interior edge 147*a*, which all cooperate to at least partially define the handle opening 149. As shown in FIG. 14, in a preferred embodiment, the first handle portion 143 includes a finger protrusion 151 that includes a finger surface 151*a* that extends between the interior edge 143*a* of the first handle portion and the interior edge 147*a* of the third handle portion 147 and at least partially defines the handle opening 149. As shown in FIG. 16, in use, a user can place their index finger against the finger surface 151*a*. The finger protrusion and surface provide a feedback point or support surface such that when a user places their index finger against the surface it helps the user with control and comfort of using the device. In a preferred embodiment, at least a portion of the finger surface 151a is straight, as shown in FIG. 14 (as opposed to the other "corners" of the handle opening 149 being rounded.

Figure 14A:
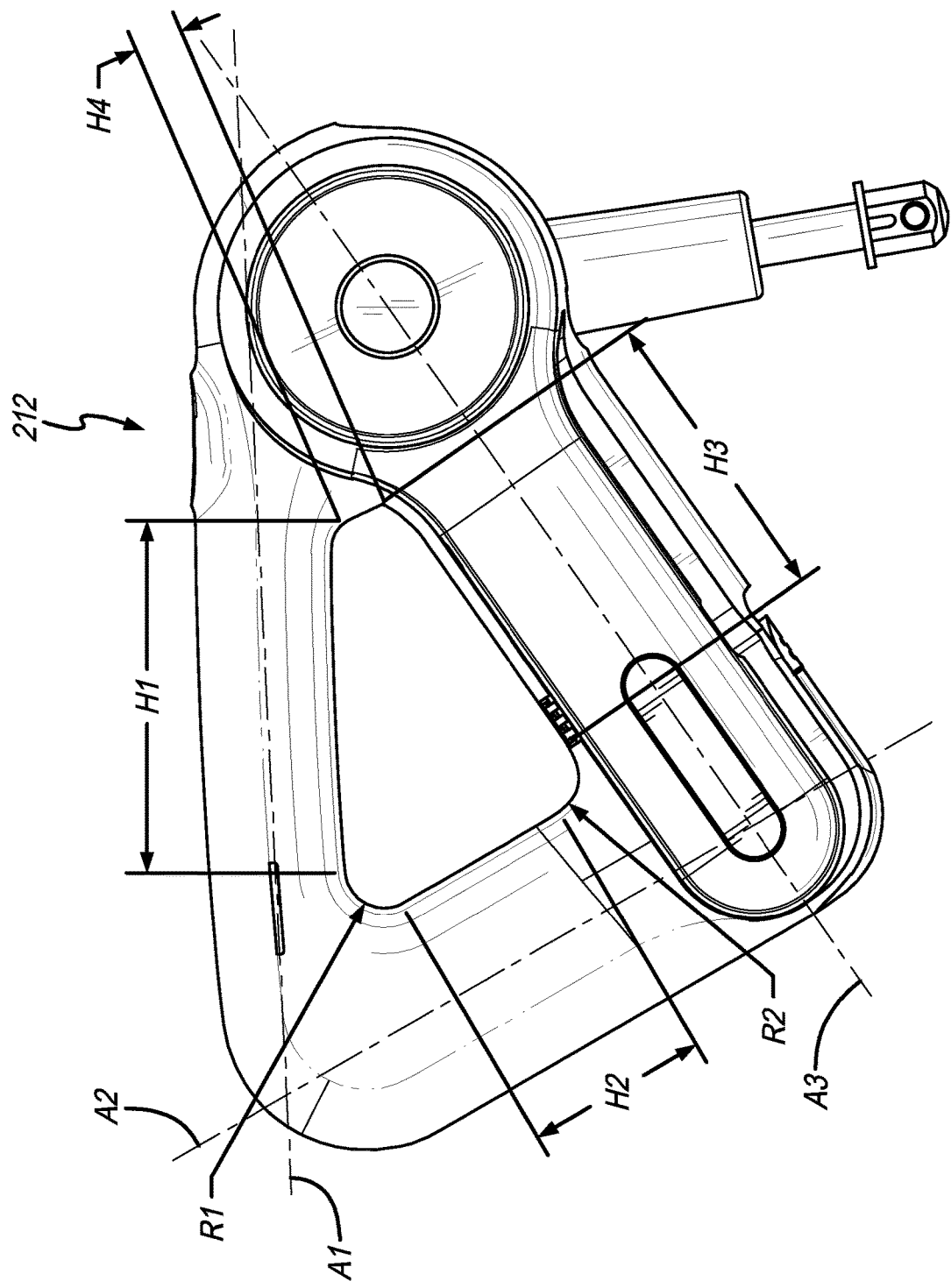
FIG. 14A is another side elevational view of the percussive massage device of FIG. 14.

FIG. 14A shows the preferred dimensions of the interior surfaces of the handle opening 149. It will be appreciated that the interior surfaces comprise a series of flat and curved surfaces. H1 is the dimension of the interior edge 143a of the first handle portion 143 (the first handle portion length). H2 is the dimension of the interior edge 145a of the second handle portion 145f (the second handle portion length). H3 is the dimension of the interior edge 147a of the third handle portion 147 (the third handle portion length). H4 is the dimension of the finger surface 151a (the finger protrusion length). R1 is the dimension of the radius between interior edges 143a and 145a and R2 is the dimension of the radius between interior edges 145a and 147a. In a preferred embodiment, H1 is about 94 mm, H2 is about 66 mm, H3 is about 96 mm, H4 is about 12 mm, R1 is about 6.5 mm and R2 is about 6.5 mm, which provides an arc length of about 10.2 mm. In the context herein, "about" is within 5 mm. In a preferred embodiment, the length of the interior edge of the handle opening is about 289 mm. The length of the interior edge of the handle opening can be between about 260 mm and about 320 mm, with any combination of H1, H2, H3, H4, R1 and R2. It will be appreciated that these dimensions are optimized so that a 95th percentile male can grip any of the three handle portions with at least three and preferably four fingers extending through the handle opening to utilize the device. It will be appreciated that any or all of surfaces R1 and R2 can be considered a part of any of the three adjacent handle portions. As shown in FIGS. 14 and 14A, with the finger surface 151a being straight, the first handle portion interior surface, second handle portion interior surface, third handle portion interior surface and finger surface cooperate to define a quadrilateral with radii or rounded edges between each of the straight surfaces.

Device 212 also includes multiple speed settings (preferably 1500 and 2400 RPM, but can be any speed or frequency taught herein). Furthermore, those of ordinary skill in the art will appreciate that although the RPM is listed as a specific number that, due to manufacturing tolerances, the RPM may oscillate during use. For example, at the 2400 RPM setting the RPM may actually oscillate between 2260 and 2640.

Figure 19:
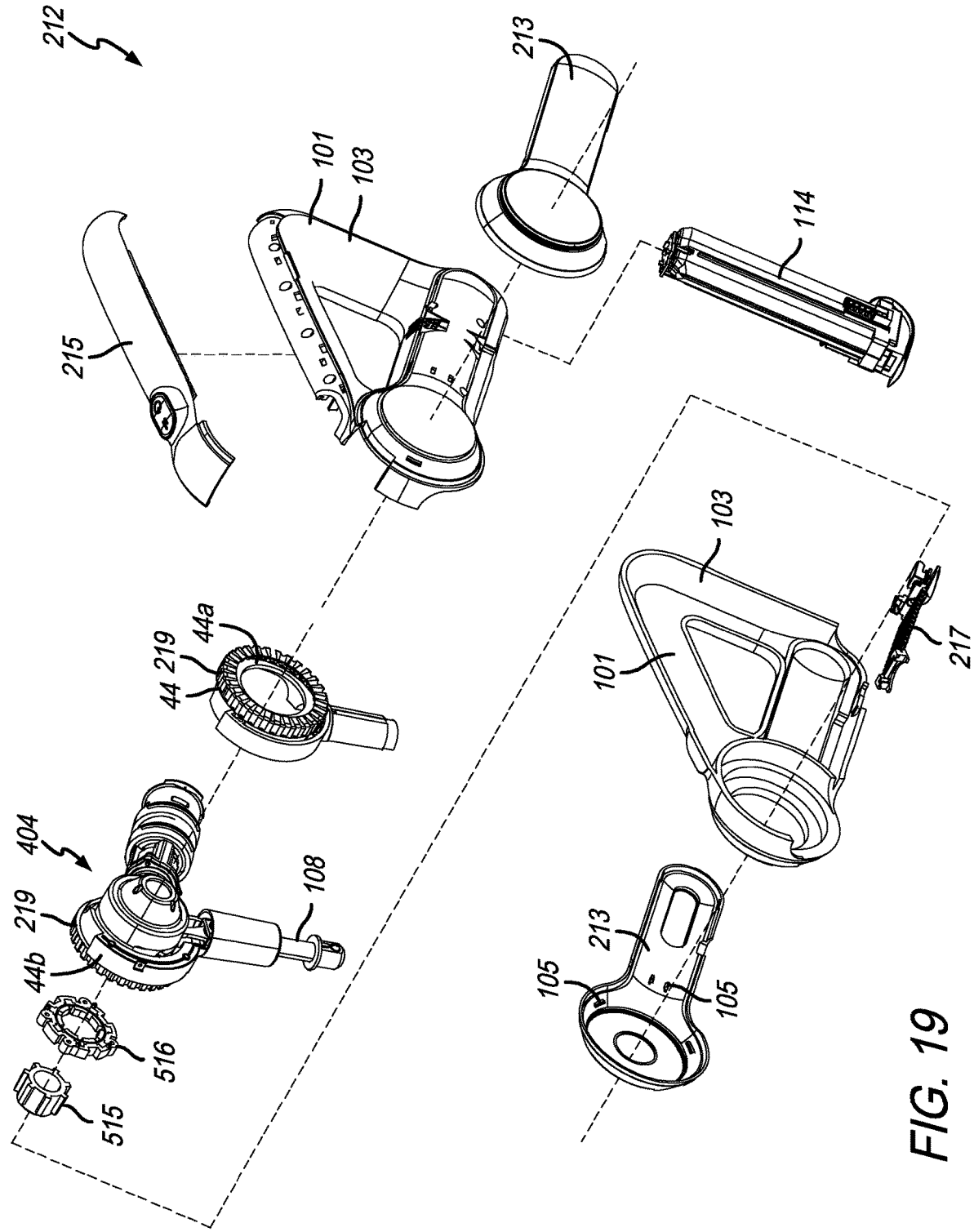
FIG. 19 is an exploded perspective view of the percussive massage device.

FIGS. 19-23 show some of the interior and exterior components that are included in the treatment devices 212 (208 and 210) shown in FIGS. 14-18 and 24-27. As shown in FIG. 19, the percussive massage device 212 includes a housing 101 that is comprised of first and second housing halves 103. Outer covers 213 and top cover 215 are received on and connected to the first and second housing halves 103, via tabs 105 or other mechanism or attachment method (e.g., threaded fasteners, clips, adhesive, sonic welding, etc.). The percussive massage device 212 also includes a tambour door 217, battery 114, inner suspension rings 219 and rotation housing 44 (with first and second rotation housing halves 44a and 44b) that houses the gearbox 404.

Figure 20:
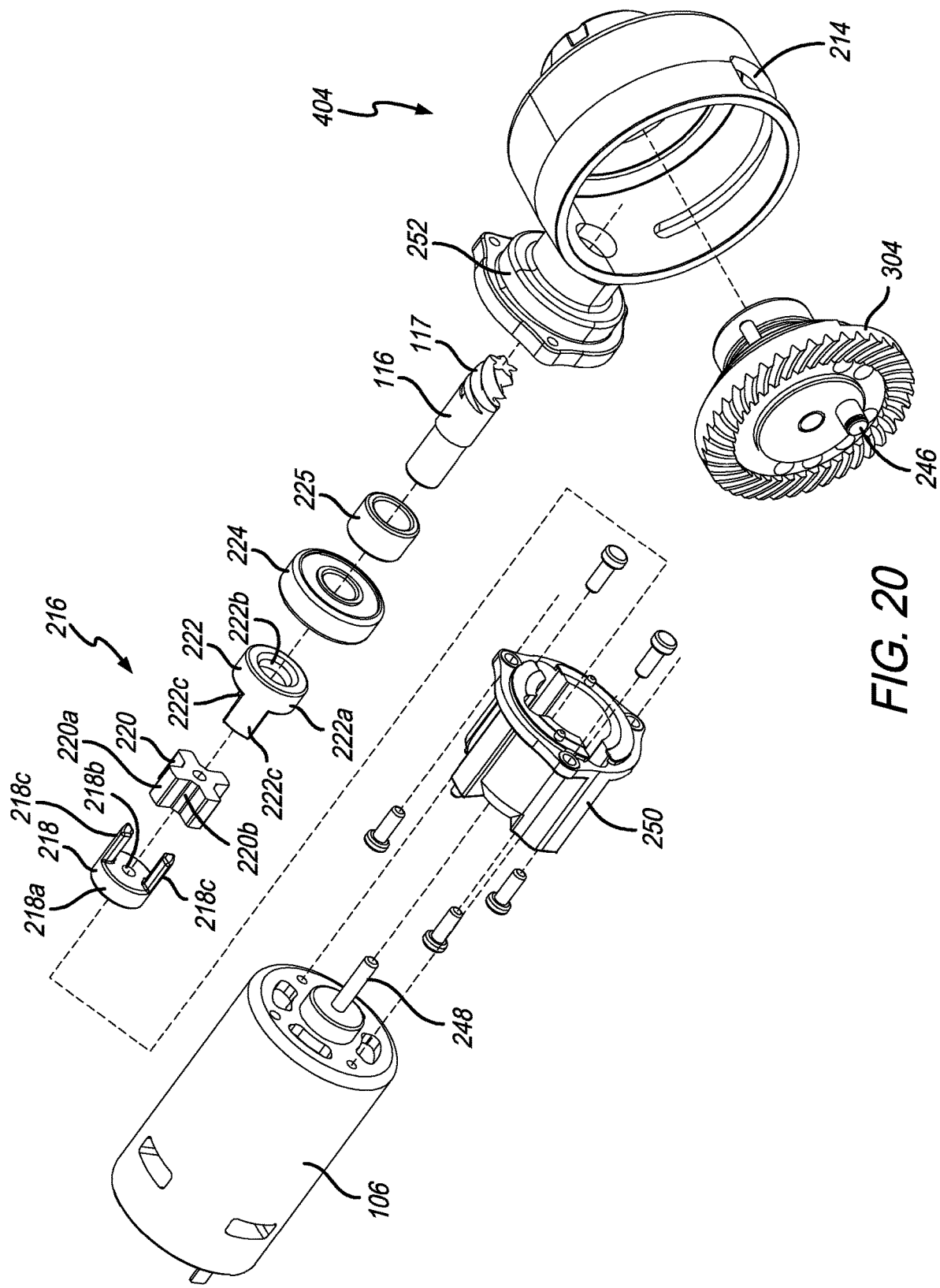
FIG. 20 is an exploded perspective view of a portion of the drive train components of the percussive massage device.

As shown in FIG. 20, the device includes a pinion coupling assembly 216 (similar to the compliant shaft damper 302 described above) that is disposed between the motor and the pinion shaft or shaft gear 117 (located on the shaft or pinion shaft 116). The pinion coupling assembly 216 is used to couple the motor to the gearbox so that the torque is fully transmitted, such that there is no radial movement and the vibrations and noise are minimized. The pinion coupling assembly 216 preferably includes three separate components, a lower connector 218, a cross coupling 220 and an upper connector 222. In a preferred embodiment, the lower connector 218 includes a main body portion 218a that defines a central opening 218b that receives the motor shaft 248 and first and second lower connector arms 218c extending outwardly from the main body portion 218a. The upper connector 222 includes a main body portion 222a that defines a central opening 222b that receives the pinion shaft 117 and first and second upper connector arms 222c extending outwardly from the main body portion 222a. Preferably, the cross coupling 220 includes radially extending ribs 220a that define channels 220b therebetween. The first and second lower connector arms 218c and the first and second upper connector arms 222c are sized and shaped to be received in the channels 220b to operatively engage the radially extending ribs. In use, the motor shaft 248 rotates the pinion coupling assembly, which rotates the pinion shaft 117. These components work together to reduce noise and vibration. In a preferred embodiment, the lower and upper connectors are made of plastic and the cross coupling is made of an elastomer. In a preferred embodiment, the cross coupling 220 is made of rubber that includes a hardness where vibrations generated by the motor are isolated while keeping the strength and transmitting the torque efficiently (without significant energy dissipation). However, the materials are not a limitation on the present invention.

In a preferred embodiment, the pinion shaft 116 is received in and extends through bearings 224 and 225. Preferably, bearing 224 includes ball bearings (and provides radial support) and bearing 225 includes needle bearings (and provides radial support, but can withstand higher temperatures). The pinion coupling assembly 216 is housed in motor mount 250, which is connected to the motor 106 and through which the motor shaft 248 extends. The motor mount 250 is connected to the gear box mount 252, as shown in FIG. 22.

Figure 21:
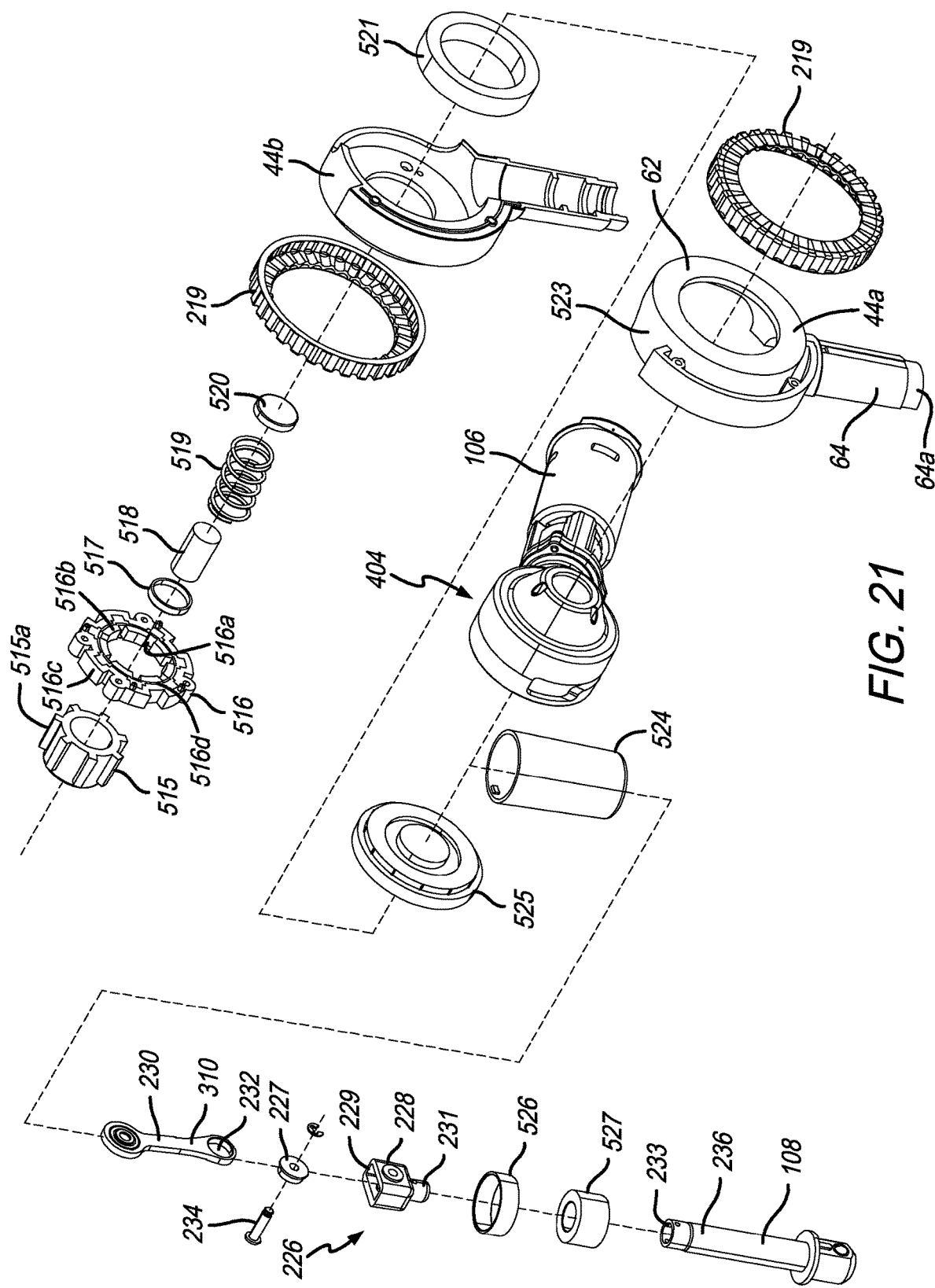
FIG. 21 is another an exploded perspective view of a portion of the percussive massage device.
Figure 22:
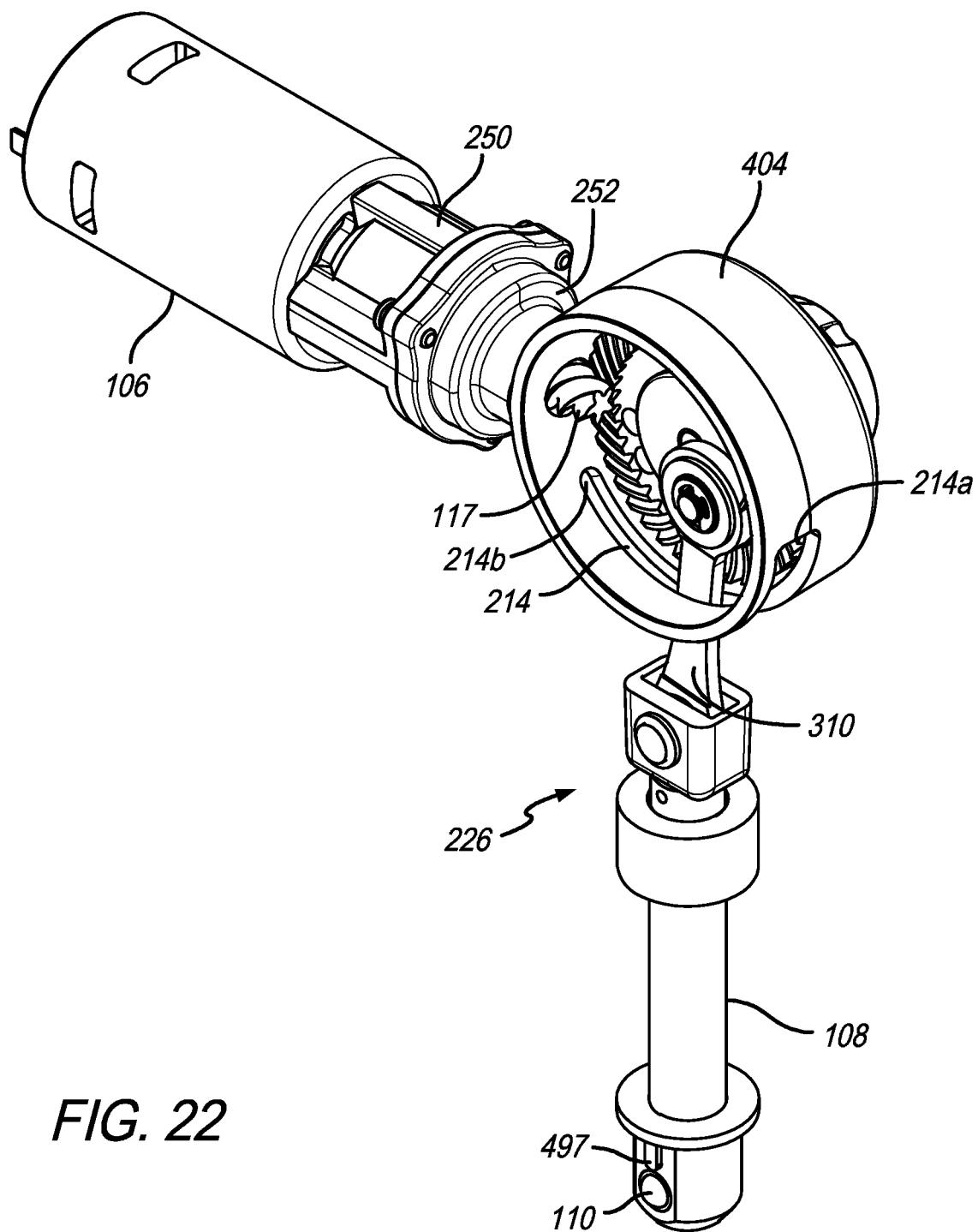
FIG. 22 is a perspective view of the drive train components of the percussive massage device.

As shown in FIGS. 20-22, the gearbox 404, in one embodiment, includes the gear member 304 and the reciprocator or push rod 230/310. Preferably, the gear member 304 includes a shaft 246 extending therefrom to which the reciprocator 310 is connected. The gearbox 404 may provide mounting points for the gear member 304 and the reciprocator 310. The gearbox 404 may restrict the motion of the gear member 304 and the reciprocator to certain directions or rotational axes. The gearbox 404 may be mounted to the housing 101. In some embodiments, the gearbox 404 is separated from the housing 101 by the one or more compliant dampening blocks 402.

As shown in FIGS. 19 and 21, in a preferred embodiment, to prevent the gearbox from transmitting vibrations to the housing a rubber cover can be provided. Further inner suspension rings 219 isolate vibration of the gearbox from handle and the treatment structures. Preferably, the rings 219 are made of an elastomer and act as a cushion to dampen vibrations between the rotation housing and the housing 101. In a preferred embodiment, the inner suspension rings 219 surround the outer radial surface of the main body portion 62 (see seat surface 523 in FIG. 21).

In one embodiment, rotation of the actuated output or shaft 108 may be selectively locked and unlocked by a user. For example, the user may unlock rotation of the shaft 108, rotate the actuated output 108 to a desired position relative to the housing 101, lock rotation of the actuated output 108, and operate the reciprocating treatment device 100. FIG. 21 shows the components that allow rotation of the rotation housing 44 together with the push rod assembly 108 and related components. Button 515 includes radially extending teeth 515a and is biased outwardly by spring 519, which surrounds and is seated on spacer 518 (which is preferably made of foam). Spring 519 is seated against dampening members 520 and 517, which are preferably made of rubber to dampen any vibrations of the spring 519. The assembly also includes a gear box cover 525 and dampening ring 521. Button 515 is outwardly biased by spring 519 to a position where teeth 515a are engaged with teeth 516a, which are defined hoop 516, which is connected to housing 101. Preferably hoop 516 includes inner and outer plastic rings 516b and 516c that sandwich a rubber ring 516d therebetween to help dampen vibrations and reduce noise. The button 515 is movable between a first position where teeth 515a are engaged with teeth 516a and a second position where teeth 515 are not engaged with teeth 516a. When the button 515 is in the first position, the rotation assembly 47 cannot rotate. When the button is pushed to the second position, the teeth 515a disengage from teeth 516a, thereby allowing the entire rotation assembly 47 to rotate. The rotation housing 44 includes a main body portion 62 disposed in the housing and an arm portion 64 extending through the rotation space 60 and outside the housing. The arm portion 64 rotates within the rotation space 60 defined in the housing 101. As shown in FIG. 15, in a preferred embodiment, the device 212 includes a tambour door 217 that unfolds within the rotation space 60 as the rotation assembly is moved from the position shown in FIG. 14 to the position shown in FIG. 15. The tambour door 217 covers slot 214. As shown in FIG. 15, an arm cover 524 covers the arm portion 64 of the rotation housing 44.

As shown in FIG. 22, the gearbox housing 404 includes a clearance slot 214 defined therein for the push rod assembly 108. The slot 214 is provided so the push rod assembly 108 can move freely and allow the rotation housing 44 to articulate. The clearance slot 214 has first and second ends 214a and 214b. As shown in FIG. 22, the push rod assembly 108 extends through the clearance slot 214. it will be appreciated that when the rotation housing 44 is rotated from a first position to a second position the push rod assembly 108 moves within the clearance slot 214 from the first end to the second end thereof.

Figure 23:
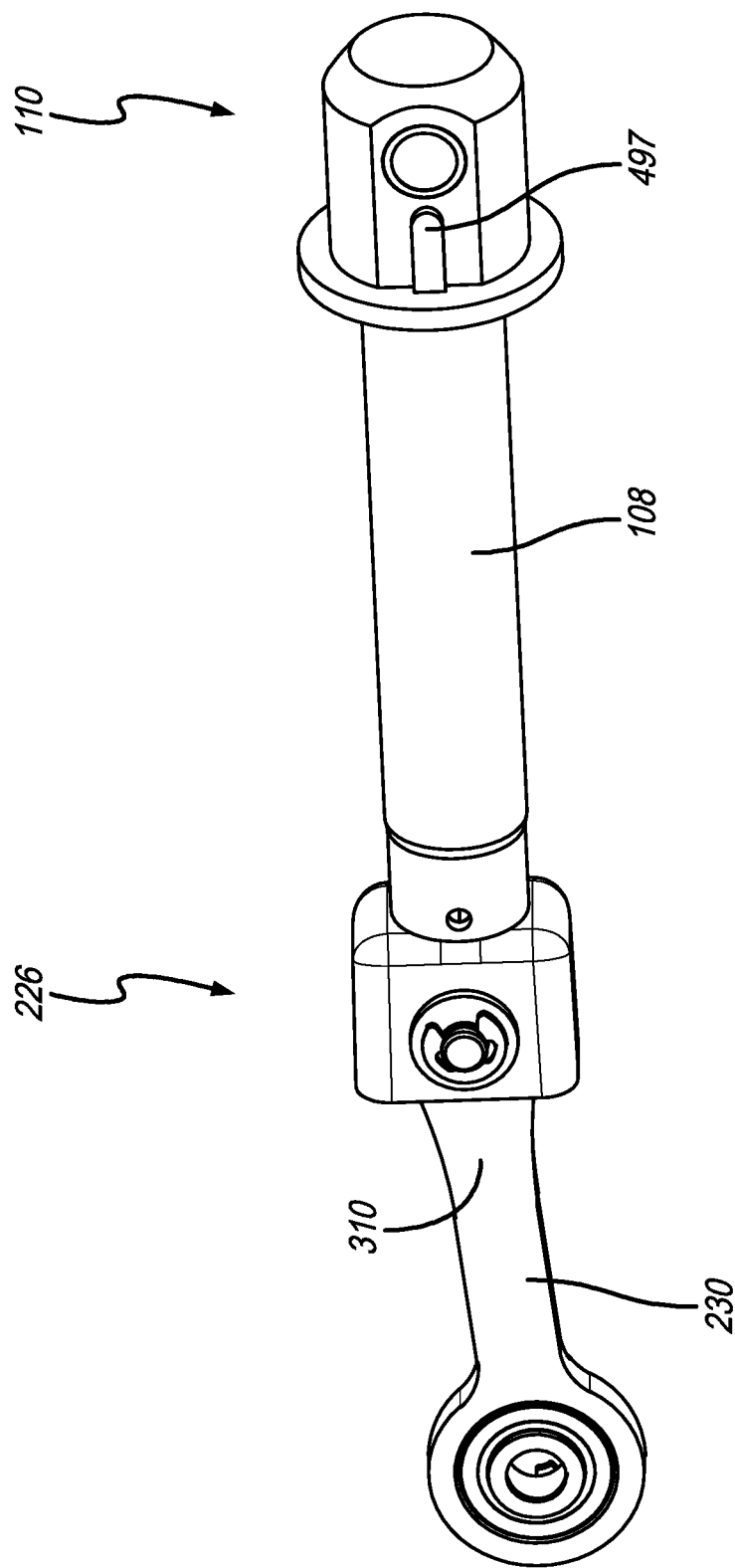
FIG. 23 is a perspective view of the push rod assembly of the percussive massage device.
Figure 24:
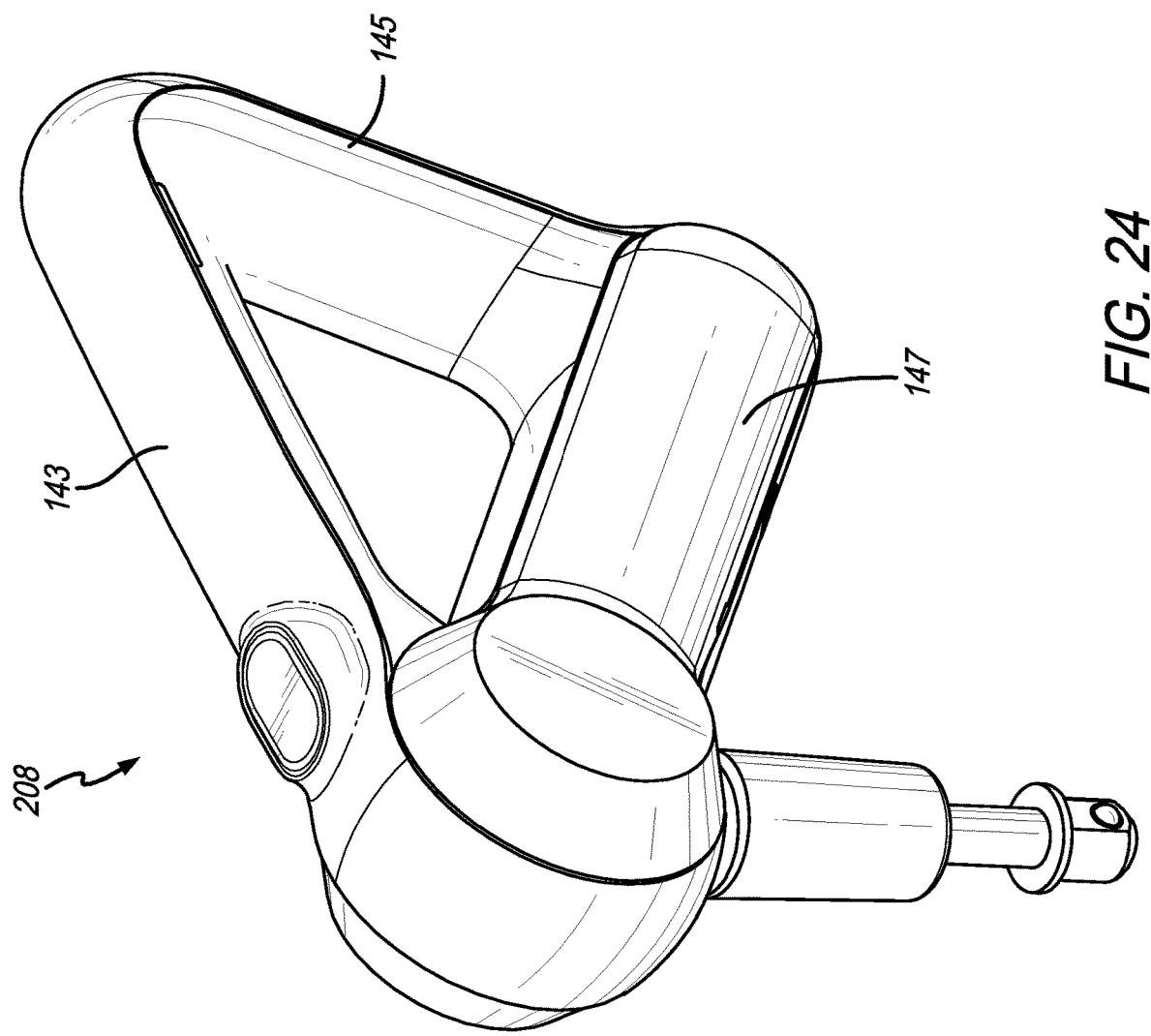
FIG. 24 is a perspective view of another percussive massage device.
Figure 25:
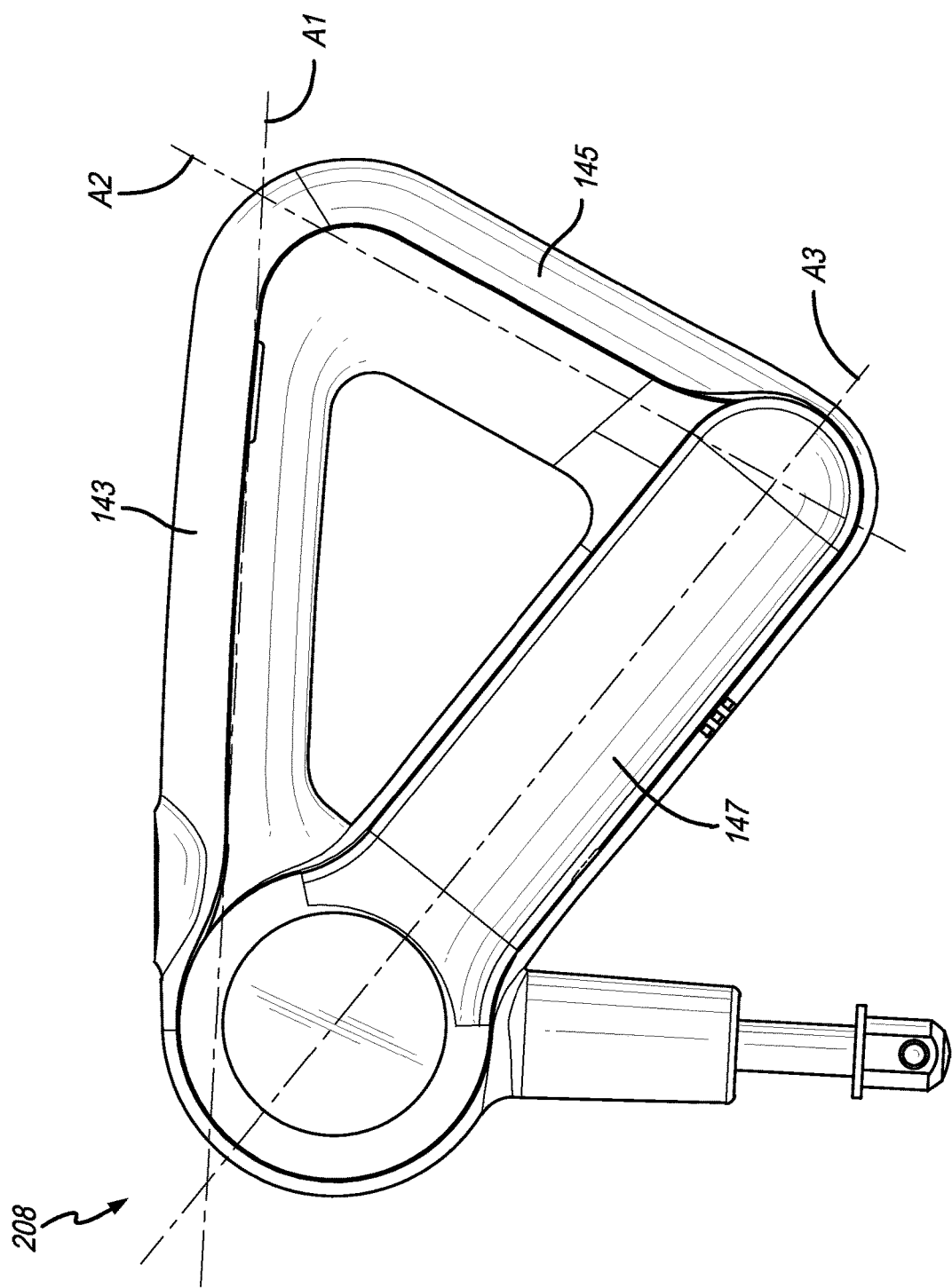
FIG. 25 is a side elevational view of the percussive massage device of FIG. 24.

As shown in FIGS. 21-23, in a preferred embodiment, the pushrod assembly or output shaft 108 includes two halves or rods with an adapter member 226 therebetween to also help reduce noise and vibration. The adapter member 226 isolates the vibrations generated in the gearbox and prevents them from being transmitted down the shaft to the treatment structure. The adapter member 226 can include anti-rotation tabs to protect the push rod from user applied torque during use. The first rod portion 230 of the output shaft 108 (push rod or reciprocator 310) includes an opening 232 on an end thereof that receives a pivot pin 234. The connection between the first rod portion 230 and the adapter member 226 includes a bushing 227 with the pin 234 and elastomeric material to dampen vibrations. The end of first rod portion 230 that includes opening 232 is received in a pocket 229 in adapter member 226. The pin 234 extends through openings in the side walls of adapter member 226, through bushing 227 and through opening 232, to secure first rod portion 230 to adapter member 226. Adapter member 226 includes a protrusion 231 extending therefrom that is received in an opening 233 in an end of the second rod portion 236, to connect the adapter member 226 to the second rod portion 236. In another embodiment, the end of the second rod portion 236 can be received in an opening in the adapter member 226. In use, the size of the top opening of pocket 229 allows the first rod portion to move side to side as the opening 232 pivots on pin 234 and first rod portion 231 reciprocates. This translates to linear reciprocation of second rod portion 236. Because the bushing 227 comprises at least some elastomeric material, vibrations are dampened (and noise reduced) as the push rod assembly 108 reciprocates.

Ring 526 is seated on and surrounds the bottom portion of the arm portion 64 (see seat 64a in FIG. 21) to help hold the first and second housing halves 44a and 44b together. Washer or guide member 527 is received in the rotation housing 44 and provides stability and a path for the reciprocating push rod assembly or output shaft 108.

As shown in FIG. 22, in this embodiment, the first rod portion 230 or push rod assembly 108 extends through clearance slot 214. It will be appreciated that the term pushrod assembly includes any of the embodiments described herein and can include a shaft with an adapter member allowing pivoting between two halves or can include a single shaft that does not include any pivoting.

As shown in FIGS. 22-23, in a preferred embodiment, the male connector 110 includes an alignment tab 497 above each ball that mates with a slot in the female opening. These tabs 497 help with proper alignment with the treatment structure. See U.S. Patent App. No. 2019/0017528, the entirety of which is incorporated herein by reference.

Figure 26:
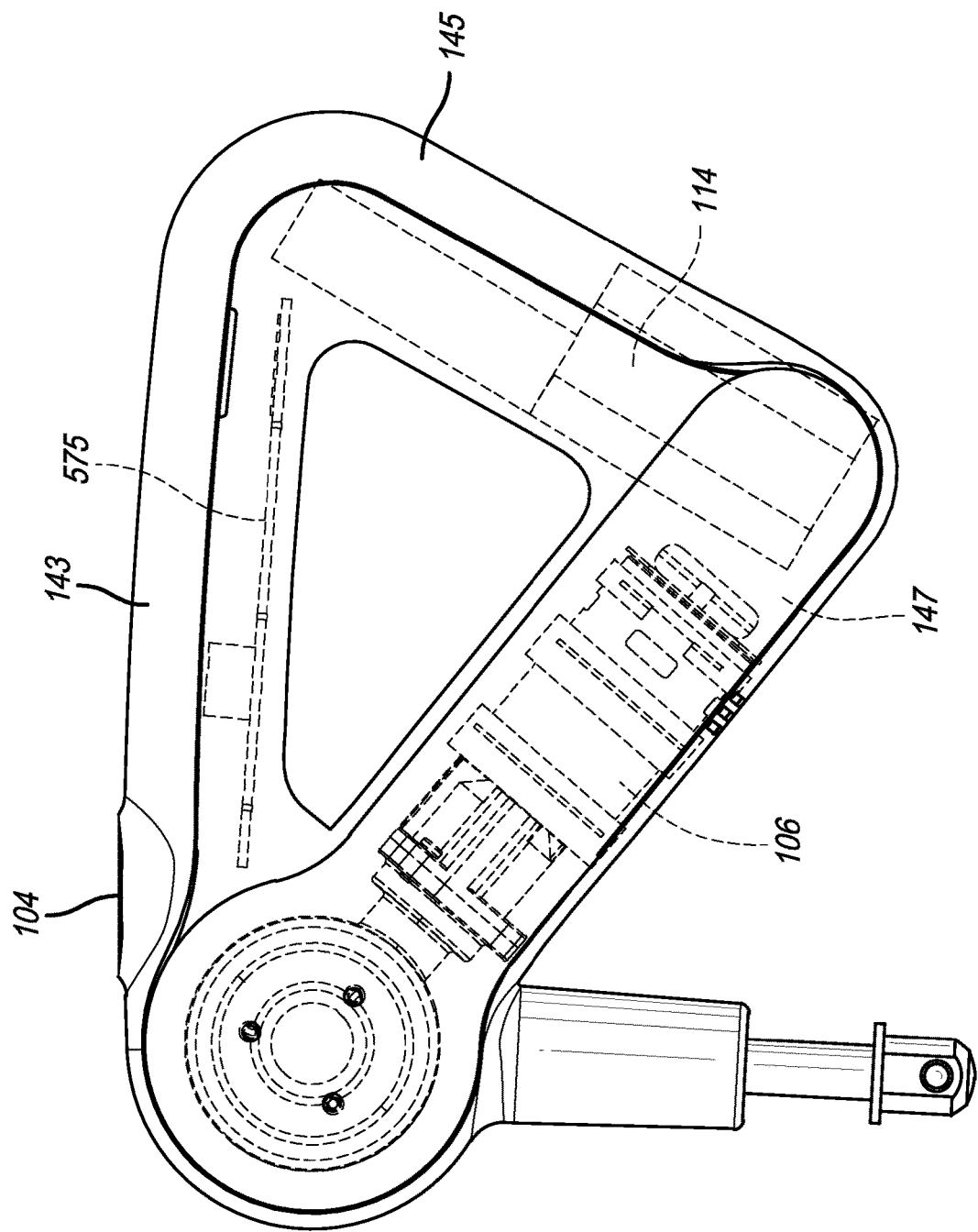
FIG. 26 is a side elevational view of the percussive massage device showing some internal components in hidden lines.
Figure 27:
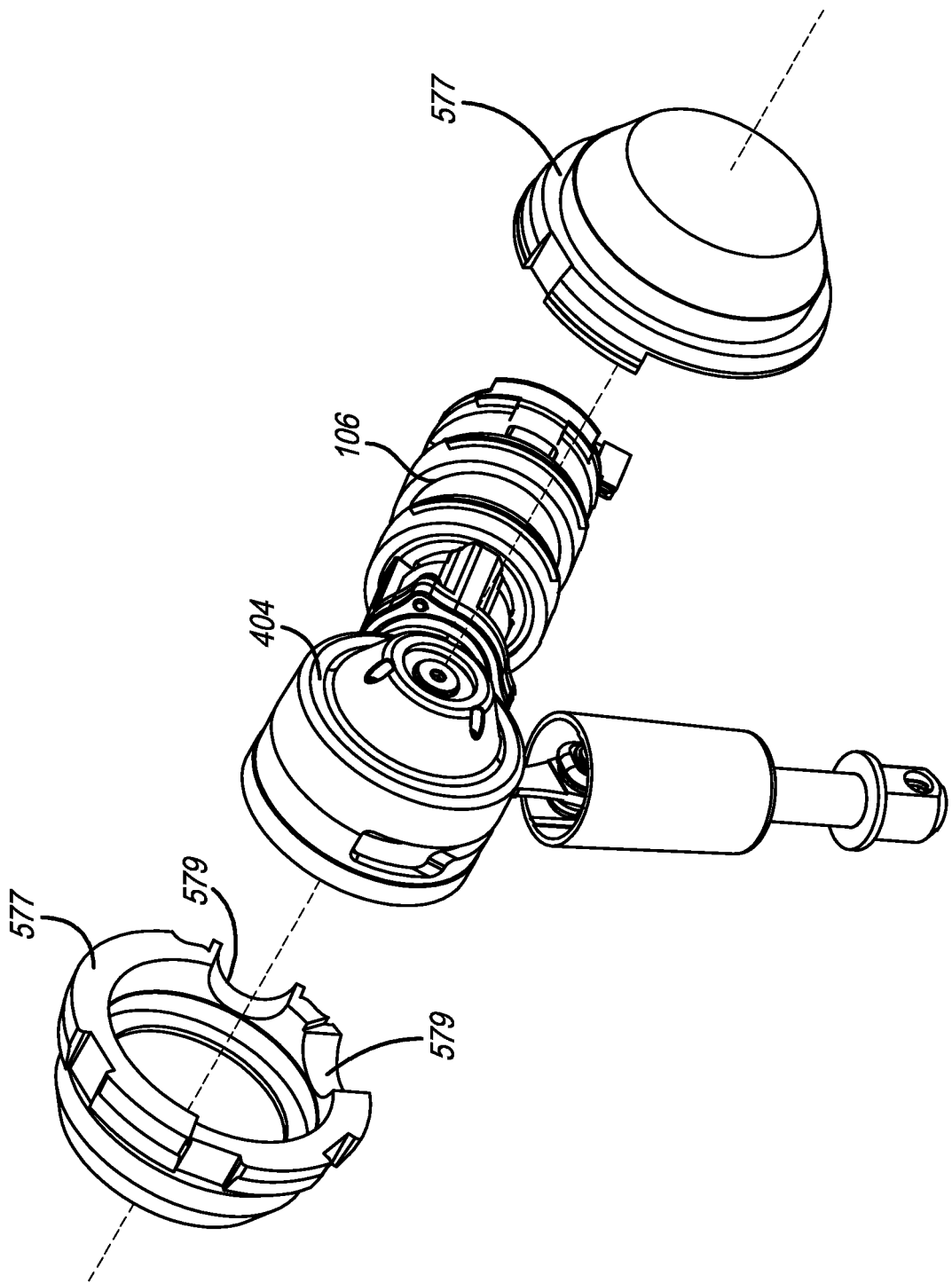
FIG. 27 is an exploded perspective view of some of the internal components of the percussive massage device.
Figure 28:
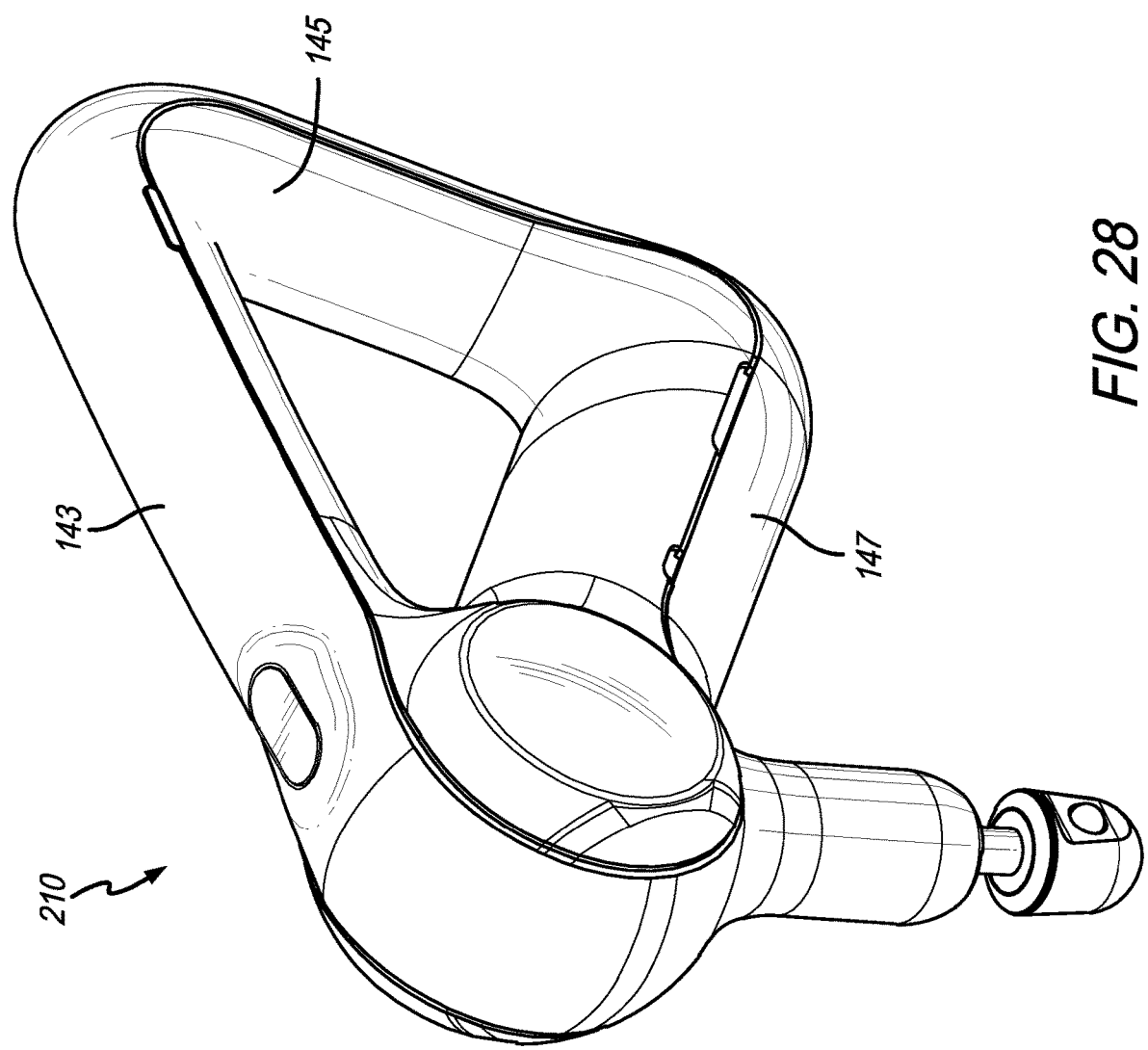
FIG. 28 is a perspective view of another percussive massage device.
Figure 29:
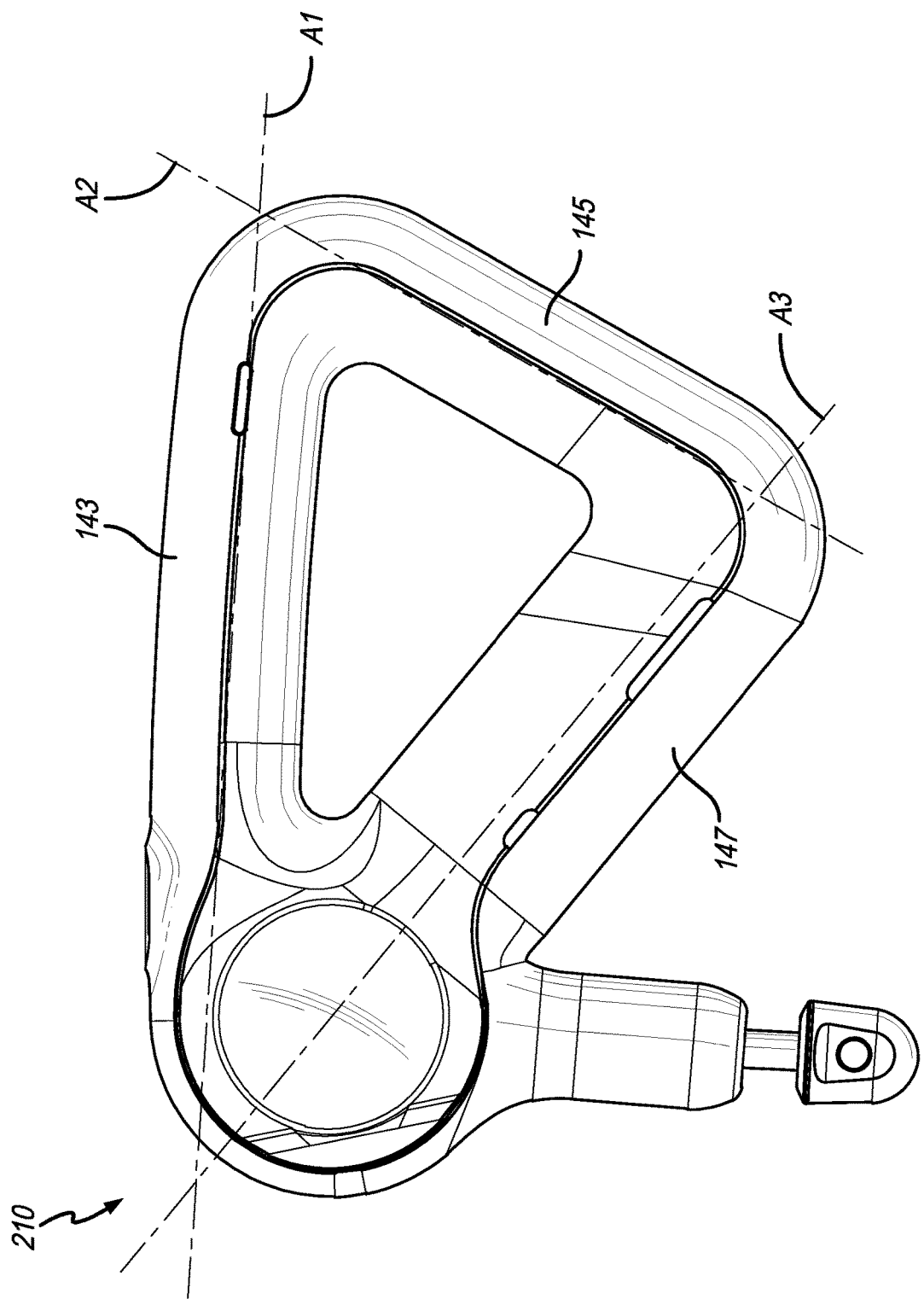
FIG. 29 is a side elevational view of the percussive massage device of FIG. 28.

FIGS. 24-29 show embodiments of percussive massage devices similar to percussive massage device 212 above, but without a rotation assembly. Device 208, shown in FIGS. 24-27 is referred to commercially as the G3. Device 210, shown in FIGS. 28-29 is referred to commercially as the LIV. As is shown in FIG. 26, in a preferred embodiment, switch 104 includes switch electronics 575 associated therewith. The switch electronics 575 may include a printed circuit board (PCB) and other components to allow the switch 104 to activate the motor 106 and to change the speed of the motor, turn the device on and off, among other tasks. As shown in FIG. 26, in a preferred embodiment, the motor 106 is housed in the third handle portion 147, the battery 114 is housed in the second handle portion 145 and the switch electronics 575 are housed in the first handle portion 143. This configuration also applies to devices 210 and 212. FIG. 27 shows cushion members 577 that surround the gearbox 404 and help dampen and reduce noise and vibration generated by the components in the gearbox. Cushion members 577 are similar to inner suspension rings 219 in device 212. However, cushion members 577 are thicker and do not need to rotate due to the exclusion of the rotation housing in devices 208 and 210. Cushion members 577 include cutouts or channels 579 therein to allow clearance of components such as the push rod assembly and pinion shaft.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges. It will be appreciated that any dimensions given herein are only exemplary and that none of the dimensions or descriptions are limiting on the present invention.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A percussive massage device comprising:
    a housing comprising first, second, and third handle portions that cooperate to at least partially define a handle opening, wherein the first handle portion defines a first axis, the second handle portion defines a second axis, and the third handle portion defines a third axis, wherein the first, second, and third axes are co-planar and cooperate to form a triangle that surrounds the handle opening, wherein the first handle portion is generally straight, wherein the second handle portion is generally straight, and wherein the third handle portion is generally straight, such that a user can grasp any of the first, second, or third handle portions independently to use the percussive massage device,
    a rechargeable battery positioned in one of the first, second, or third handle portions,
    a motor positioned in one of the first, second, or third handle portions,
    a switch for activating the motor,
    a push rod assembly operatively connected to the motor and configured to reciprocate in response to activation of the motor, wherein a distal end of the push rod assembly includes a connector thereon, and wherein a massage attachment is configured to be removably received on the connector, wherein the massage attachment includes a shaft recess that includes first and second opposing detents defined therein, wherein the connector includes first and second outwardly biased ball bearings, wherein the connecter is configured to be received in the shaft recess, the first outwardly biased ball bearing being received in the first detent and the second outwardly biased ball bearing being received in the second detent.

2. The percussive massage device of claim 1 wherein the first handle portion includes a first handle portion interior edge and defines a first handle portion length, wherein the first handle portion length is configured to be long enough that when a user grasps the first handle portion with a hand at least a portion of three fingers extend through the handle opening and contact the first handle portion interior edge, wherein the second handle portion includes a second handle portion interior edge and defines a second handle portion length, wherein the second handle portion length is configured to be long enough that when a user grasps the second handle portion with a hand at least a portion of three fingers extend through the handle opening and contact the second handle portion interior edge, wherein the third handle portion includes a third handle portion interior edge and defines a third handle portion length, wherein the third handle portion length is configured to be long enough that when a user grasps the third handle portion with a hand at least a portion of three fingers extend through the handle opening and contact the third handle portion interior edge.

3. The percussive massage device of claim 1 wherein the housing includes an arm portion, and wherein the distal end of the push rod assembly extends outside of the arm portion, such that the distal end of the push rod assembly is located exterior of the housing.

4. The percussive massage device of claim 1 wherein the first axis and the second axis form a first angle, wherein the second axis and the third axis form a second angle, and wherein the first axis and the third axis form a third angle, and wherein the first, second and third angles are all different.

5. The percussive massage device of claim 1 wherein the first handle portion includes a first handle portion exterior edge that is generally straight, wherein the second handle portion includes a second handle portion exterior edge that is generally straight, wherein the third handle portion includes a third handle portion exterior edge that is generally straight, wherein the first handle portion exterior edge defines a first handle portion exterior edge extended, wherein the second handle portion exterior edge defines a second handle portion exterior edge extended, wherein the third handle portion exterior edge defines a third handle portion exterior edge extended, wherein the first, second, and third exterior edges extended cooperate to define a triangle that surrounds the handle opening.

6. The percussive massage device of claim 1 wherein the first handle portion includes a first handle portion interior edge, wherein the second handle portion includes a second handle portion interior edge, wherein the third handle portion includes a third handle portion interior edge, wherein the first handle portion interior edge defines a first handle portion interior edge extended, wherein the second handle portion interior edge defines a second handle portion interior edge extended, wherein the third handle portion interior edge defines a third handle portion interior edge extended, wherein the first, second, and third interior edges extended cooperate to define a triangle that surrounds the handle opening.

7. The percussive massage device of claim 1, wherein the shaft recess includes first and second flat surfaces, wherein the first detent is defined in the first flat surface and the second detent is defined in the second flat surface, and wherein the connector includes first and second flat surfaces, wherein the first flat surface of the connector opposes the first flat surface of the shaft recess, and wherein the second flat surface of the connector opposes the second flat surface of the shaft recess.

8. The percussive massage device of claim 7 wherein the connector includes first and second alignment tabs located above the first and second outwardly biased ball bearings, respectively, wherein the shaft recess includes first and second slots, wherein the first alignment tab is received in the first slot and the second alignment tab is received in the first slot.

9. A method of using a percussive massage device, the method comprising the steps of:
obtaining the percussive massage device, wherein the percussive massage device includes a housing comprising first, second, and third handle portions that cooperate to at least partially define a handle opening, a rechargeable battery positioned in one of the first, second, or third handle portions, a motor positioned in one of the first, second, or third handle portions of the housing, a switch for activating the motor, a counterweight member operatively connected to the motor, wherein the counterweight member includes a counterweight and a shaft, wherein the counterweight and the shaft are configured to rotate about a rotation axis, wherein the shaft and counterweight rotate about the rotation axis, a push rod assembly operatively connected to the motor and configured to reciprocate in response to activation of the motor, wherein the push rod assembly includes a first rod portion having a proximal end and a distal end and a second rod portion having a proximal end and a distal end, wherein the proximal end of the first rod portion is connected to the shaft of the counterweight member, wherein the distal end of the first rod portion is pivotably connected to the proximal end of the second rod portion, and a massage attachment removably secured to the distal end of the second rod portion, wherein the first handle portion defines a first axis, the second handle portion defines a second axis, and the third handle portion defines a third axis, wherein the first, second, and third axes are co-planar and cooperate to form a triangle that surrounds the handle opening, wherein the first handle portion is generally straight, wherein the second handle portion is generally straight, and wherein the third handle portion is generally straight,
activating the motor using the switch,
grasping the first handle portion,
massaging a first body part,
grasping the second handle portion and massaging the first body part or a second body part, and
grasping the third handle portion and massaging the first body part, the second body part or a third body part.

10. The method of claim 9 wherein the first handle portion includes a first handle portion interior edge and defines a first handle portion length, wherein the first handle portion length is long enough that when a user grasps the first handle portion with a hand at least a portion of three fingers extend through the handle opening and contact the first handle portion interior edge, wherein the second handle portion includes a second handle portion interior edge and defines a second handle portion length, wherein the second handle portion length is long enough that when a user grasps the second handle portion with a hand at least a portion of three fingers extend through the handle opening and contact the second handle portion interior edge, wherein the third handle portion includes a third handle portion interior edge and defines a third handle portion length, wherein the third handle portion length is long enough that when a user grasps the third handle portion with a hand at least a portion of three fingers extend through the handle opening and contact the third handle portion interior edge.

11. A percussive massage device comprising:
a housing comprising first, second, and third handle portions that cooperate to at least partially define a handle opening, wherein the first handle portion defines a first axis, the second handle portion defines a second axis, and the third handle portion defines a third axis, wherein the first, second, and third axes are co-planar and cooperate to form a triangle that surrounds the handle opening, wherein the handle portions are configured such that a user can grasp any of the first, second, or third handle portions independently to use the percussive massage device, wherein the first handle portion includes a first handle portion interior edge and defines a first handle portion length, wherein the first handle portion length is configured to be long enough that when a user grasps the first handle portion with a hand at least a portion of three fingers extend through the handle opening and contact the first handle portion interior edge, wherein the second handle portion includes a second handle portion interior edge and defines a second handle portion length, wherein the second handle portion length is configured to be long enough that when a user grasps the second handle portion with a hand at least a portion of three fingers extend through the handle opening and contact the second handle portion interior edge, wherein the third handle portion includes a third handle portion interior edge and defines a third handle portion length, and wherein the third handle portion length is configured to be long enough that when a user grasps the third handle portion with a hand at least a portion of three fingers extend through the handle opening and contact the third handle portion interior edge, wherein the first handle portion, second handle portion, and third handle portion are generally straight, a rechargeable battery positioned in one of the first, second, or third handle portions, a brushless motor positioned in one of the first, second, or third handle portions, a switch for activating the motor, a counterweight member operatively connected to the motor, wherein the counterweight member includes a counterweight and a shaft, and wherein the counterweight and the shaft are configured to rotate about a rotation axis, and a push rod assembly operatively connected to the motor and configured to reciprocate in response to activation of the motor, wherein the push rod assembly includes a first rod portion having a proximal end and a distal end and a second rod portion having a proximal end and a distal end, wherein the proximal end of the first rod portion is connected to the shaft of the counterweight member, wherein the distal end of the first rod portion is pivotably connected to the proximal end of the second rod portion, wherein the distal end of the second rod portion includes a connector thereon, and wherein the connector is configured to removably receive a massage attachment.

12. The percussive massage device of claim 11 wherein the first, second, and third handle portions are oriented such that a user can grasp any of the first, second, or third handle portions independently with a single hand to use the percussive massage device at a plurality of different angles.

13. The percussive massage device of claim 11 wherein the rotation axis extends laterally through the housing, wherein the second rod portion defines a reciprocation axis, and wherein the reciprocation axis extends perpendicular to the rotation axis.

14. The percussive massage device of claim 13 wherein the housing includes a bulge portion, wherein the first handle portion extends rearwardly from the bulge portion, wherein the second handle portion extends downwardly and forwardly from the first handle portion, and wherein the third handle portion extends forwardly and upwardly from the second handle portion to the bulge portion.

15. The percussive massage device of claim 14 wherein the bulge portion includes a circular shape that defines a central axis that extends laterally through the housing, wherein the push rod assembly defines a reciprocation axis, and wherein the reciprocation axis extends perpendicular to the central axis.

16. The percussive massage device of claim 11 wherein the first handle portion includes a finger protrusion that includes a finger surface that extends between the interior edge of the first handle portion and the interior edge of the third handle portion and at least partially defines the handle opening, wherein the finger surface is straight.

\* \* \* \* \*